United States Patent
Ohta et al.

(10) Patent No.: US 10,617,394 B2
(45) Date of Patent: *Apr. 14, 2020

(54) ULTRASOUND DIAGNOSTIC APPARATUS, METHOD OF PRODUCING ULTRASOUND IMAGE

(71) Applicant: FUJIFILM Corporation, Tokyo (JP)

(72) Inventors: Yasunori Ohta, Ashigara-kami-gun (JP); Tsuyoshi Tanabe, Ashigara-kami-gun (JP); Noriaki Ida, Ashigara-kami-gun (JP); Shin Nakata, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 936 days.

This patent is subject to a terminal disclaimer.

(21) Appl. No.: 15/217,618

(22) Filed: Jul. 22, 2016

(65) Prior Publication Data

US 2016/0324504 A1 Nov. 10, 2016

Related U.S. Application Data

(62) Division of application No. 14/161,042, filed on Jan. 22, 2014, now Pat. No. 9,421,000.

(30) Foreign Application Priority Data

Jan. 22, 2013 (JP) .................................. 2013-009274

(51) Int. Cl.
*A61B 8/00* (2006.01)
*A61B 8/08* (2006.01)
*A61B 8/14* (2006.01)

(52) U.S. Cl.
CPC ............ *A61B 8/5207* (2013.01); *A61B 8/145* (2013.01); *A61B 8/4488* (2013.01); *A61B 8/461* (2013.01);

(Continued)

(58) Field of Classification Search
CPC ...... A61B 8/5207; A61B 8/145; A61B 8/5269; A61B 8/5223; A61B 8/469; A61B 8/467; A61B 8/461; A61B 8/4488; A61B 8/54
See application file for complete search history.

(56) References Cited

U.S. PATENT DOCUMENTS 9,757,094 B2 *  9/2017 Ohta .................... A61B 8/5207
9,907,532 B2 *  3/2018 Ohta ........................ A61B 8/08
(Continued)

FOREIGN PATENT DOCUMENTS

JP       8-154930 A       6/1996
JP    2008-264531 A     11/2008
(Continued)

OTHER PUBLICATIONS

Japanese Office Action, dated Jan. 6, 2015, for Japanese Application No. 2013-009274, including a partial English translation.

*Primary Examiner* — Joel Lamprecht
(74) *Attorney, Agent, or Firm* — Birch, Stewart, Kolasch & Birch, LLP

(57) ABSTRACT

Ultrasonic transmission and reception for sound speed setting is performed in response to an instruction to freeze, an instruction on an observation target range, an instruction to change image quality and an instruction to change an image mode, a reception signal obtained by the ultrasonic transmission and reception for sound speed setting is used to set the sound speed in a subject, and a reception signal obtained during ultrasonic transmission and reception is processed based on the set sound speed to produce an ultrasound image. Such method makes it possible to produce a high-quality ultrasound image subjected to delay correction appropriate to various operations on an ultrasound diagnostic apparatus, such as freezing and change in image quality.

11 Claims, 9 Drawing Sheets

(52) U.S. Cl.
CPC .............. *A61B 8/467* (2013.01); *A61B 8/469* (2013.01); *A61B 8/5223* (2013.01); *A61B 8/5269* (2013.01); *A61B 8/54* (2013.01)

(56) References Cited

U.S. PATENT DOCUMENTS

| | | |
|---|---|---|
| 2008/0242999 A1 | 10/2008 | Kakee |
| 2010/0331692 A1 | 12/2010 | Kakee et al. |
| 2012/0259225 A1 | 10/2012 | Tashiro |
| 2013/0303912 A1 | 11/2013 | Katsuyama |

FOREIGN PATENT DOCUMENTS

| | | |
|---|---|---|
| JP | 2009-61086 A | 3/2009 |
| JP | 2009-101145 A | 5/2009 |
| JP | 2010-119481 A | 6/2010 |
| JP | 2011-25010 A | 2/2011 |
| JP | 2011-92686 A | 5/2011 |
| JP | 2011-252276 A | 12/2011 |
| JP | 2012-161569 A | 8/2012 |
| JP | 2012-217611 A | 11/2012 |
| WO | WO 2011-001867 A1 | 1/2011 |

\* cited by examiner

FIG. 8A
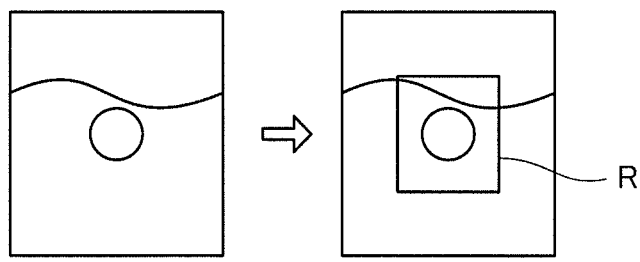
FIG. 8B
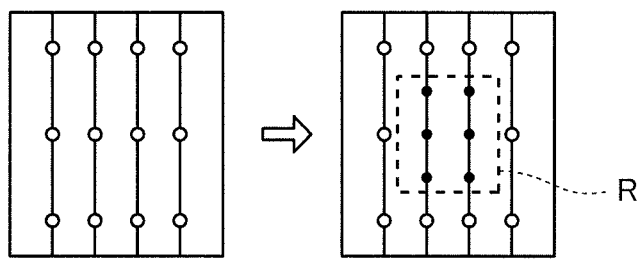
FIG. 9A    FIG. 9B    FIG. 9C
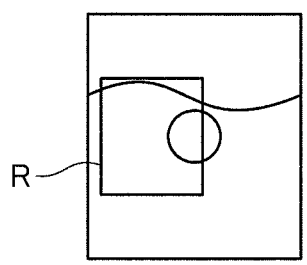 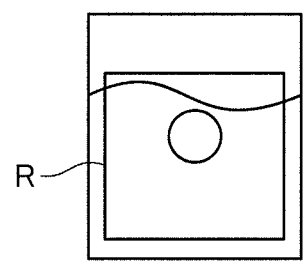 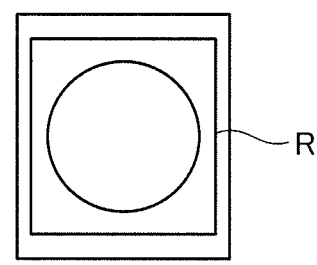
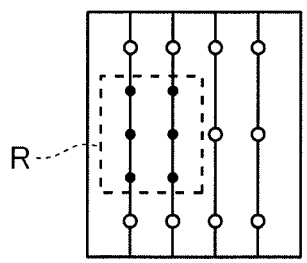 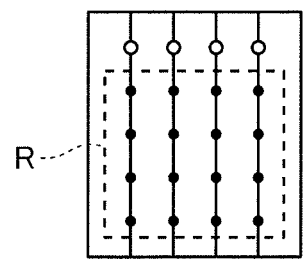 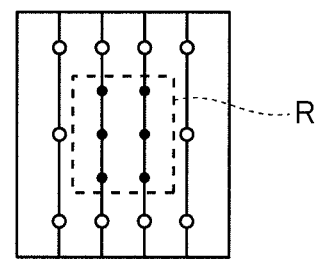

ULTRASOUND DIAGNOSTIC APPARATUS, METHOD OF PRODUCING ULTRASOUND IMAGE

This application is a Divisional of copending application Ser. No. 14/161,042, filed on Jan. 22, 2014, which claims priority under 35 U.S.C. §119(a) to Application No. 2013-009274, filed in Japan on Jan. 22, 2013, all of which are hereby expressly incorporated by reference into the present application.

BACKGROUND OF THE INVENTION

The present invention relates to an ultrasound diagnostic apparatus. Specifically, the present invention relates to an ultrasound diagnostic apparatus which allows stable display of a high-quality ultrasound image when various operations, such as freeze and change of image quality, are performed in the ultrasound imaging apparatus, a method of producing an ultrasound image, and a recording medium.

An ultrasound diagnostic apparatus using an ultrasound image has hitherto been put into practical use in the field of medicine.

In general, this type of ultrasound diagnostic apparatus is composed of an ultrasound probe (hereinafter, referred to as a probe) which has a piezoelectric element array in which piezoelectric elements to perform transmission and reception of ultrasonic waves are arranged, and a diagnostic apparatus body.

In the ultrasound diagnostic apparatus, an ultrasonic wave is transmitted from the probe toward a subject, an ultrasonic echo from the subject is received by the probe, and the reception signal is electrically processed in the diagnostic apparatus body to produce an ultrasound image.

In the piezoelectric element array of the ultrasound probe, an ultrasonic echo by single transmission of an ultrasonic beam is received by a plurality of piezoelectric elements. Accordingly, even if the ultrasonic echo is reflected at the same reflection point, the time until the ultrasonic echo enters each piezoelectric element differs depending on the position of the piezoelectric element.

For this reason, in the ultrasound diagnostic apparatus, delay correction using a delay time according to the position or the like of each piezoelectric element is performed on the reception signal output from the ultrasound probe, phase focusing is made by the delay correction, and phasing addition is performed to produce a sound ray signal (sound ray data), thereby producing an appropriate ultrasound image with no distortion.

The delay correction is performed using a sound speed of an ultrasonic wave (hereinafter, also simply referred to as "sound speed") in the subject. In conventional the ultrasound diagnostic apparatus, on the assumption that the sound speed is constant, the value of the ultrasonic wave sound speed set as the whole of the apparatus is fixed to a certain value (for example, 1530 m/sec).

However, since the sound speed differs due to a difference of a tissue, such as a fat layer or a muscle layer in a living body, the sound speed of the ultrasonic wave in the subject is not uniform. Further, a stout subject and a thin subject are different from each other in the thickness of the fat layer or the muscle layer.

For this reason, in the conventional ultrasound apparatus in which the sound speed of the ultrasonic wave is fixed, the difference between the actual sound speed in the subject and the set sound speed often occurs.

If the set sound speed is different from the actual sound speed, it is not possible to accurately perform the delay correction. As a result, there is a problem in that image quality of the ultrasound image is deteriorated, for example, the produced ultrasound image is distorted with respect to the actual subject.

In contrast, JP 2011-92686 A describes an ultrasound diagnostic apparatus in which regions of interest are set so as to divide the inside of the subject (ultrasound image) into a plurality of regions, and a sound speed is set for each of the regions of interest. Specifically, in this apparatus, the transmission and reception of an ultrasonic wave for forming a transmission focus corresponding to a region of interest is performed, delay correction or phasing addition is performed by setting a plurality of sound speeds to calculate the focus index (for example, sharpness or the like) of the region of interest, and the sound speed at which the highest focus index is obtained is set as the sound speed in the region of interest.

According to an ultrasound diagnostic apparatus described in JP 2011-92686 A, an accurate sound speed is set corresponding to an individual difference of the subject, each of the sites in the subject, or the like, and delay correction is performed, thereby producing a high-quality ultrasound image with no distortion or the like.

The sound speed of the subject changes depending on the state of a tissue, such as a muscle. In addition, change in the position of the probe causes change in the sound speed of the subject in a region with which the probe is in contact. Accordingly, in order to stably obtain an ultrasound image of high-quality, it is desirable to appropriately update (reset) the sound speed.

On the other hand, in the ultrasound diagnostic apparatus, when setting the sound speed, many operations are required. That is, a frequent update of the sound speed imposes a heavy burden on the ultrasound diagnostic apparatus. For this reason, in the ultrasound diagnostic apparatus, the update of the sound speed is performed at a reasonable regular timing, for example, once at a predetermined time interval (once for every predetermined number of frames).

Meanwhile, as is well known, in the ultrasound diagnostic apparatus, in order to favorably perform the observation of the ultrasound image, various instructions can be given to the ultrasound image displayed on a display.

For example, while the ultrasound image is basically a motion image, that is, a live image, in the ultrasound diagnostic apparatus, in order to perform the observation of an intended site in detail, a FREEZE button (freeze switch) which instructs the display of a still image, instead of a motion image, is provided.

The ultrasound diagnostic apparatus is also provided with region of interest (ROI) setting means or observation depth setting means so as to instruct an observation target range (observation region) of the ultrasound image.

In addition, the ultrasound diagnostic apparatus is provided with gain (amplification and attenuation of the reception signal) adjustment means so as to change image quality (luminance) of the ultrasound image. An apparatus which can change image quality for each observation depth is also known.

Moreover, the ultrasound image has various image modes. For example, the ultrasound image has image modes such as a fundamental image mode in which according to a center frequency of an ultrasonic wave to be received, the center frequencies of ultrasonic waves to be transmitted and received are identical, a tissue harmonic mode in which an ultrasonic echo of a harmonic of a transmitted ultrasonic wave is received to produce an ultrasound image, a compound harmonic mode in which an ultrasonic echo having the same center frequency as that of a transmitted ultrasonic wave and a harmonic of the transmitted ultrasonic wave are received to perform image synthesis, and the like, and the ultrasound diagnostic apparatus is configured such that a desired mode can be selected and instructed.

Such various instructions (operations) are performed for some purpose.

For example, the instruction of freeze, the instruction to set an ROI, and the instruction to change an observation depth are made so as to observe a specific region in the subject in more detail. The change of image quality or the change of the image mode is instructed so as to observe an observation site in detail with an ultrasound image of higher-quality or an ultrasound image more suitable for the observation.

However, as described above, since a frequent update of the sound speed imposes a heavy burden on the ultrasound diagnostic apparatus, the update of the sound speed is performed at a reasonable regular timing. For this reason, in the ultrasound diagnostic apparatus, there are many cases where the sound speed which is set when various instructions are performed is different from the actual sound speed of the subject.

As a result, in spite of an ultrasound image desired to be observed in detail, deterioration of image quality, such as distortion, may occur in the displayed ultrasound image.

SUMMARY OF THE INVENTION

The present invention has been accomplished in order to solve the drawbacks in the prior art, and an object thereof is to provide an ultrasound diagnostic apparatus, a method of producing an ultrasound image, and a recording medium which can stably display an ultrasound image of high-quality even when various instructions, such as an instruction of freeze, an instruction to change in an observation target range, an instruction to change image quality, an instruction to change an image mode, and the like are given in an ultrasound diagnostic apparatus.

In order to achieve such object, the present invention provides an ultrasound diagnostic apparatus comprising: a piezoelectric element array which has piezoelectric elements arranged therein, each piezoelectric element configured to transmit an ultrasonic wave, to receive an ultrasonic echo reflected by a subject, and to output a reception signal according to a received ultrasonic wave; a controller which controls ultrasonic transmission and reception by the piezoelectric element array; a storage which stores the reception signal output from the piezoelectric element array; a sound speed setter which sets a sound speed in the subject using the reception signal stored in the storage; an image producer which processes the reception signal output from the piezoelectric element array or the reception signal read from the storage, based on the sound speed set by the sound speed setter to produce an ultrasound image; a display; and an operating device which has a freeze instruction inputter configured to instruct to display a still image on the display, an observation target range instruction inputter configured to specify an observation target range of an ultrasound image displayed on the display, an image quality change instruction inputter configured to instruct to change image quality of the ultrasound image, and a mode change instruction inputter configured to instruct to change an image mode of the ultrasound image, wherein:

the controller causes the piezoelectric element array to perform ultrasonic transmission and reception for sound speed setting so as to allow the sound speed setter to set the sound speed in response to at least one instruction out of an instruction to display a still image from the freeze instruction inputter, an instruction on the observation target range from the observation target range instruction inputter, an instruction to change image quality from the image quality change instruction inputter, and an instruction to change an image mode from the mode change instruction inputter; the sound speed setter sets the sound speed in the subject using a reception signal obtained by the ultrasonic transmission and reception for sound speed setting to update the sound speed; the image producer processes the reception signal output from the piezoelectric element array based on an updated sound speed to produce an ultrasound image; and the display displays the ultrasound image produced by processing based on the updated sound speed.

In the inventive ultrasound diagnostic apparatus as such, it is preferable that the controller causes the piezoelectric element array to perform the ultrasonic transmission and reception for sound speed setting in response to any instruction out of the instruction to display a still image from the freeze instruction inputter, the instruction on the observation target range from the observation target range instruction inputter, the instruction to change image quality from the image quality change instruction inputter, and the instruction to change an image mode from the mode change instruction inputter.

Preferably, the controller causes the piezoelectric element array to perform the ultrasonic transmission and reception for sound speed setting immediately after the instruction is given.

The sound speed setter preferably divides the subject into a plurality of regions and sets the sound speed for each region, and the image producer preferably processes the reception signal based on the sound speed set for each region to produce an ultrasound image.

It is preferable that the image producer processes the reception signal obtained by the ultrasonic transmission and reception for sound speed setting based on the updated sound speed to produce an ultrasound image in response to the instruction to display a still image from the freeze instruction inputter.

It is also preferable that the image producer processes a reception signal output from the piezoelectric element array during ultrasonic transmission and reception before the ultrasonic transmission and reception for sound speed setting based on the updated sound speed to produce an ultrasound image in response to the instruction to display a still image from the freeze instruction inputter.

Preferably, the image producer processes a reception signal output from the piezoelectric element array at least during ultrasonic transmission and reception immediately before the ultrasonic transmission and reception for sound speed setting based on the updated sound speed to produce an ultrasound image.

It is preferable that, in response to the instruction to display a still image from the freeze instruction inputter, the image producer processes a reception signal output from the piezoelectric element array during ultrasonic transmission and reception before the ultrasonic transmission and reception for sound speed setting based on the updated sound speed to produce an ultrasound image after update of the sound speed, and processes the reception signal based on a sound speed set before the update of the sound speed to produce an ultrasound image before the update of the sound speed, and the display displays the ultrasound image after the update of the sound speed and the ultrasound image before the update of the sound speed.

Preferably, the operating device has a selection instruction inputter configured to select either the ultrasound image after the update of the sound speed or the ultrasound image before the update of the sound speed, and, when selection is made by the selection instruction inputter, the display only displays the ultrasound image as selected.

The observation target range instruction inputter preferably includes either or both of an observation depth change instruction inputter configured to instruct change in observation depth and a region of interest setting instruction inputter configured to instruct setting of a region of interest.

It is preferable that the region of interest setting instruction inputter has a region of interest determination instruction inputter configured to instruct determination of a region of interest and, when a region of interest is determined through the region of interest determination instruction inputter, the controller, considering that the instruction on the observation target range is given, causes the piezoelectric element array to perform the ultrasonic transmission and reception for sound speed setting.

It is also preferable that the region of interest setting instruction inputter has a region of interest movement instruction inputter configured to instruct movement of a region of interest and a region of interest size change instruction inputter configured to instruct change in size of a region of interest and, when no operation is performed through the region of interest movement instruction inputter or the region of interest size change instruction inputter for a predetermined time in a state where the setting of a region of interest is instructed, the controller, considering that the instruction on the observation target range is given, causes the piezoelectric element array to perform the ultrasonic transmission and reception for sound speed setting.

It is preferable that the observation depth change instruction inputter has an extension and reduction instruction inputter configured to increase and decrease the observation depth, and the sound speed setter updates the sound speed only for a region extended or reduced through the extension and reduction instruction inputter configured to increase and decrease the observation depth.

It is preferable that, when the instruction on the observation target range is given by the observation target range instruction inputter, the controller causes the piezoelectric element array to perform the ultrasonic transmission and reception for sound speed setting to form a transmission focus for sound speed setting corresponding to the observation target range thus specified, and the sound speed setter sets and updates the sound speed in the subject according to the observation target range thus specified.

It is preferable that the image quality change instruction inputter instructs to change image quality of the ultrasound image for a predetermined region and, when change in image quality for the predetermined region is instructed by the image quality change instruction inputter, the controller causes the piezoelectric element array to perform, with respect to the predetermined region, the ultrasonic transmission and reception for sound speed setting so as to allow the sound speed setter to set the sound speed, whereupon the sound speed setter preferably sets a sound speed in the predetermined region using the reception signal obtained by the ultrasonic transmission and reception for sound speed setting to update the sound speed.

It is preferable that change in image quality of the ultrasound image according to the instruction to change image quality from the image quality change instruction inputter is performed by either or both of change of an amplification factor for amplifying the reception signal and image processing in the image producer.

Preferably, the image quality change instruction inputter has a function of instructing the change in image quality for each depth region set in advance and, when a depth region for which image quality is to be changed is specified by an instruction from the image quality change instruction inputter, the sound speed setter only updates the sound speed in the specified depth region.

It is also preferable that the image quality change instruction inputter has at least one of a gain adjustment instruction inputter configured to adjust gain of an ultrasound image, a dynamic range adjustment instruction inputter configured to adjust dynamic range of an ultrasound image, a gradation curve processing instruction inputter configured to process gradation curve of an ultrasound image, a sharpness adjustment instruction inputter configured to adjust sharpness of an ultrasound image, and a speckle noise removal processing instruction inputter configured to instruct removal of speckle noise from an ultrasound image.

The image mode is preferably any of a fundamental wave mode, a tissue harmonic mode, and a compound harmonic mode.

The image producer preferably processes the reception signal obtained by the ultrasonic transmission and reception for sound speed setting based on the updated sound speed to produce an ultrasound image.

The present invention also provides a method of producing an ultrasound image, the method comprising the steps of: performing ultrasonic transmission and reception for sound speed setting so as to set a sound speed in a subject in response to at least one instruction out of an instruction to freeze to display a still image, an instruction on an observation target range of an ultrasound image, an instruction to change image quality of an ultrasound image, and an instruction to change an image mode of an ultrasound image; setting the sound speed in the subject using a reception signal obtained by the ultrasonic transmission and reception for sound speed setting; processing an ultrasonic reception signal based on the sound speed to produce an ultrasound image; and displaying the ultrasound image.

In the inventive method of producing an ultrasound image as such, it is preferable that, if any instruction out of the instruction to freeze to display a still image, the instruction on an observation target range of an ultrasound image, the instruction to change image quality of an ultrasound image, and the instruction to change an image mode of an ultrasound image is given, the ultrasonic transmission and reception for sound speed setting is performed and the sound speed in the subject is set.

The ultrasonic transmission and reception for sound speed setting is preferably performed immediately after the instruction is given, so as to set the sound speed in the subject.

Preferably, the sound speed is set for each region obtained by dividing the subject into a plurality of regions, and the ultrasound image is produced based on the sound speed set for each region.

The present invention also provides a recording medium having recorded thereon a program for making an ultrasound diagnostic apparatus display an ultrasound image, the program causing a computer to execute: a transmission and reception step of performing ultrasonic transmission and reception for sound speed setting so as to set a sound speed in a subject in response to at least one instruction out of an instruction to freeze to display a still image, an instruction on an observation target range of an ultrasound image, an instruction to change image quality of an ultrasound image, and an instruction to change an image mode of an ultrasound image; a sound speed setting step of setting the sound speed in the subject using a reception signal obtained in the transmission and reception step; an image production step of processing an ultrasonic reception signal based on the sound speed set in the sound speed setting step to produce an ultrasound image; and a display step of displaying the ultrasound image produced in the image production step on a display.

In the inventive recording medium as such, it is preferable that, in the transmission and reception step of the program, the ultrasonic transmission and reception for sound speed setting is performed in response to any instruction out of the instruction to freeze to display a still image, the instruction on an observation target range of an ultrasound image, the instruction to change image quality of an ultrasound image, and the instruction to change an image mode of an ultrasound image.

Preferably, in the transmission and reception step of the program, the ultrasonic transmission and reception for sound speed setting is performed immediately after the instruction is given.

The program is preferably such that, in the sound speed setting step, the sound speed is set for each region obtained by dividing the subject into a plurality of regions, and in the image production step, the ultrasound image is produced based on the sound speed set for each region.

According to the invention, in an ultrasound diagnostic apparatus, the sound speed of the subject is updated in accordance with an instruction to display a still image by a FREEZE button; an instruction of an observation target range, such as ROI setting or change in observation depth; an instruction to change image quality, such as gain adjustment; an instruction to change an image mode such as change from a fundamental image mode, in which the center frequencies of ultrasonic waves to be transmitted and received are identical, to a tissue harmonic mode; or the like, and an ultrasound image is produced using the updated sound speed.

Therefore, according to the present invention, it is possible to display an ultrasound image of high-quality based on an accurate sound speed corresponding to various instructions in terms of an ultrasound image desired to be observed in detail.

BRIEF DESCRIPTION OF THE DRAWINGS

FIGS. 8A and 8B are conceptual diagrams illustrating another example of update of a sound speed in the ultrasound diagnostic apparatus shown in FIG. 1.

FIGS. 9A to 9C are conceptual diagrams illustrating another example of update of a sound speed in the ultrasound diagnostic apparatus shown in FIG. 1.

DETAILED DESCRIPTION OF THE INVENTION

Hereinafter, an ultrasound diagnostic apparatus, a method of producing an ultrasound image, and a recording medium of the invention will be described in detail on the basis of preferred examples described in the accompanying drawings.

Figure 1:
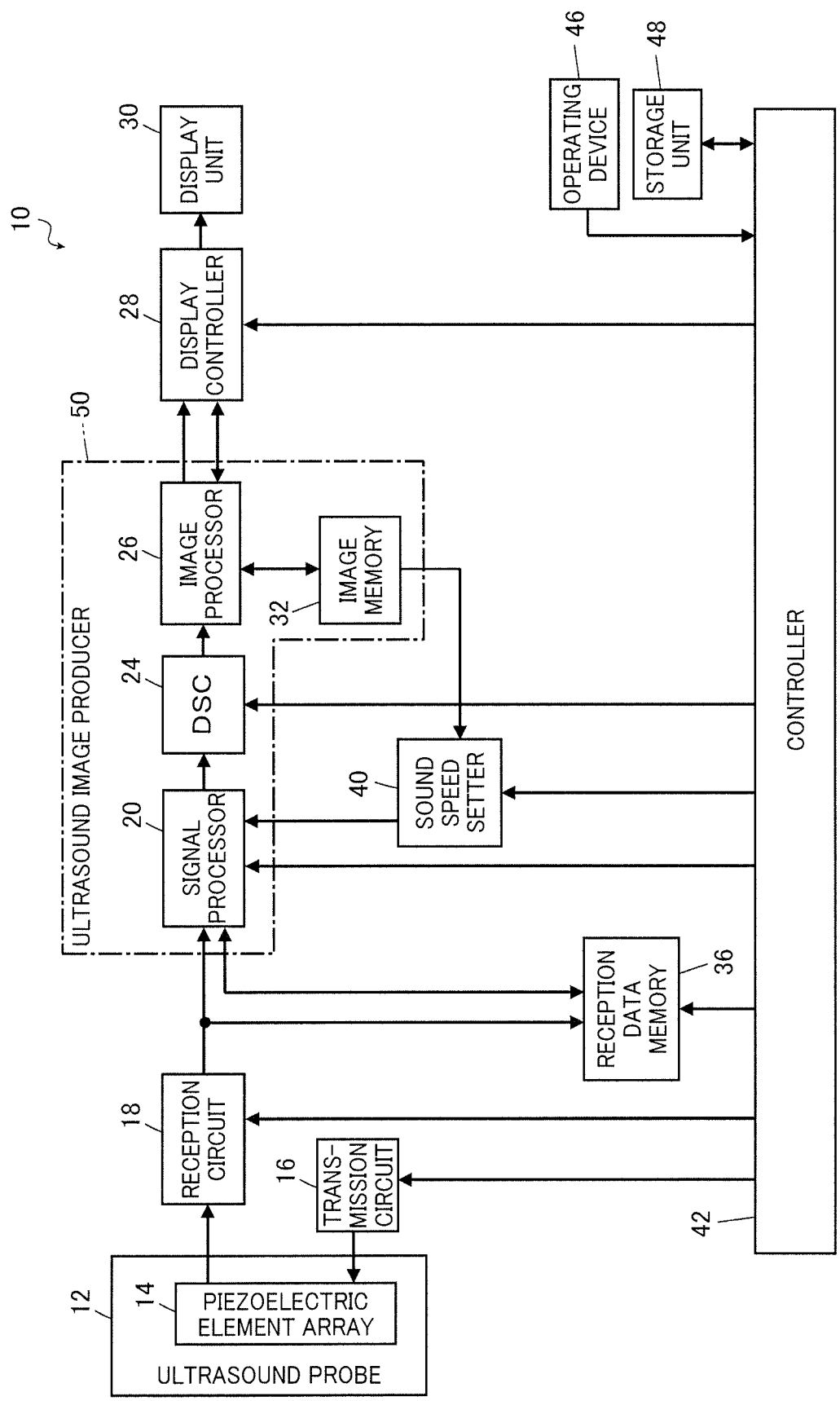
FIG. 1 is a block diagram conceptually showing an ultrasound diagnostic apparatus of the invention.

FIG. 1 is a block diagram conceptually showing an example of an ultrasound diagnostic apparatus of the invention which executes a method of producing an ultrasound image of the invention.

As shown in FIG. 1, an ultrasound diagnostic apparatus 10 has an ultrasound probe 12 (hereinafter, referred to as a probe 12) which includes a piezoelectric element array 14.

A transmission circuit 16 and a reception circuit 18 are connected to the piezoelectric element array 14 of the probe 12. A signal processor 20, a digital scan converter (DSC) 24, an image processor 26, a display controller 28, and a display unit 30 are sequentially connected to the reception circuit 18. An image memory 32 is connected to the image processor 26.

An ultrasound image producer 50 is constituted by the signal processor 20, the DSC 24, the image processor 26, and the image memory 32.

A reception data memory 36 is connected to the reception circuit 18 and the signal processor 20, and a sound speed setter 40 is connected to the image memory 32 and the signal processor 20.

Further, a controller 42 is connected to the transmission circuit 16, the reception circuit 18, the signal processor 20, the DSC 24, the display controller 28, the reception data memory 36, and the sound speed setter 40. An operating device 46 and a storage unit 48 are connected to the controller 42.

In the illustrated example, the transmission circuit 16, the reception circuit 18, the ultrasound image producer 50, the display controller 28, the display unit 30, the reception data memory 36, the sound speed setter 40, the controller 42, the operating device 46, and the storage unit 48 constitute a diagnostic apparatus body of the ultrasound diagnostic apparatus 10.

The diagnostic apparatus body is constituted using, for example, a computer or the like.

The piezoelectric element array 14 has a plurality of piezoelectric elements (ultrasound transducers) arranged in a one-dimensional or two-dimensional manner. Each of the piezoelectric elements transmits an ultrasonic wave in accordance with a driving signal supplied from the transmission circuit 16, receives an ultrasonic echo from a subject, and outputs a reception signal.

The piezoelectric element is constituted by a vibrator in which electrodes are formed at both ends of a piezoelectric substance. Examples of the piezoelectric substance include piezoelectric ceramic represented by PZT (lead zirconate titanate), a polymer piezoelectric element represented by PVDF (polyvinylidene difluoride), piezoelectric single crystal represented by PMN-PT (lead magnesium niobate-lead titanate solid solution), and the like.

If a pulsed or continuous-wave voltage is applied across the electrodes of the vibrator, the piezoelectric substance expands and contracts, whereby pulsed or continuous-wave ultrasonic waves are produced from the respective vibrators, and the ultrasonic waves are synthesized to form an ultrasonic beam.

When receiving the ultrasonic waves, the vibrators expand and contract to produce electric signals. The electric signals are output from the respective piezoelectric elements of the piezoelectric element array 14 as the reception signals of the ultrasonic waves.

The transmission circuit 16 includes, for example, a plurality of pulse generators. The transmission circuit 16 adjusts the delay amount of each of the driving signals on the basis of a transmission delay pattern selected in accordance with a control signal from the controller 42 such that the ultrasonic waves transmitted from the piezoelectric element array 14 form an intended ultrasonic beam, and supplies the driving signals to a plurality of piezoelectric elements.

The reception circuit 18 has a plurality of amplifiers and A/D converters, and the like. The reception circuit 18 amplifies and A/D converts the reception signals transmitted from the respective piezoelectric elements of the piezoelectric element array 14, and produces digitized reception data corresponding to the number of reception channels.

The amplifier of the reception circuit 18 may perform gain adjustment (brightness adjustment) of an ultrasound image according to operation of an STC key 68 or a GAIN dial 114 described later, in addition to a predetermined amplification of reception signal. At this time, the amplifier of the reception circuit 18 changes the overall amplification factor (gain) in accordance with operation of the GAIN dial 114, and changes the amplification factor in a corresponding depth region (that is, reception time) in accordance with operation of the STC key 68.

Here, under the control by the controller 42 described later, the transmission circuit 16 and the reception circuit 18 cause the piezoelectric element array 14 to perform transmission and reception of an ultrasonic wave for sound speed setting for allowing the sound speed setter 40 to set the sound speed of an ultrasonic wave in the subject at a predetermined timing, for example, once for every predetermined number of frames.

If an instruction of freeze by a FREEZE button 116 provided in the operating device 46, an instruction of gain adjustment by the GAIN dial 114, or the like is performed similarly under the control by the controller 42, the transmission circuit 16 and the reception circuit 18 cause the piezoelectric element array 14 to perform transmission and reception of an ultrasonic wave for sound speed setting for allowing the sound speed setter 40 to set a sound speed in a subsequent frame (preferably, a frame immediately after the instruction).

In this regard, detailed description will be provided later.

The signal processor 20 carries out delay correction on reception data produced by the reception circuit 18 on the basis of the sound speed (a set sound speed and an optimum sound speed described later) input from the sound speed setter 40 to produce delay correction data. Then, the signal processor 20 performs reception focusing processing by adding delay correction data (phasing addition). With this processing, the focus of the ultrasonic echo is narrowed to produce a sound ray signal (sound ray data).

Further, the signal processor 20 performs correction of attenuation due to distance in accordance with the depth of the reflection point of the ultrasonic wave on the sound ray signal, and then performs envelope detection processing to produce a B-mode image signal (ultrasound image) which is tomographic image information relating to the tissue in the subject.

The signal processor 20 may perform the gain adjustment of the ultrasound image according to operation of the STC key 68 or the GAIN dial 114 described later.

The DSC 24 converts (raster-converts) the B-mode image signal produced by the signal processor 20 to an image signal based on a normal television signal scanning system.

The image processor 26 performs various kinds of necessary image processing, such as gradation processing, on the B-mode image signal input from the DSC 24, and then outputs the B-mode image signal subjected to image processing to the display controller 28. Alternatively, the image processor 26 stores the B-mode image signal subjected to the similar image processing in the image memory 32. The image processor 26 may perform the gain adjustment of the ultrasound image according to operation of the STC key 68 or the GAIN dial 114 described later. That is, in the ultrasound diagnostic apparatus 10, the gain adjustment of the ultrasound image according to operation of the STC key 68 or the GAIN dial 114 may be performed by at least one of adjustment of the amplification factor in the amplifier of the reception circuit 18, image processing in the signal processor 20, and image processing in the image processor 26. The gain adjustment of the ultrasound image by image processing may be performed by a known method.

As described above, the ultrasound image producer 50 is constituted by the signal processor 20, the DSC 24, the image processor 26, and the image memory 32.

The display controller 28 controls the display unit 30 to display the ultrasound image or the like on the basis of the B-mode image signal subjected to image processing in the image processor 26 or various kinds of information input by the operating device 46.

The display unit 30 includes, for example, a display, such as an LCD, and displays the ultrasound image under the control of the display controller 28.

The reception data memory 36 sequentially stores reception data output from the reception circuit 18, and also stores delay correction data produced in the signal processor 20.

The sound speed setter 40 sets the sound speed (optimum sound speed described later) of the ultrasonic wave in the subject.

In the present invention, as an example, the sound speed setter 40 gives a predetermined set sound speed to the signal processor 20, and changes the set sound speed to cause the ultrasound image producer 50 to produce the B-mode image signal. Then, the sound speed setter 40 analyzes each B-mode image produced at each set sound speed, and sets a sound speed which gives maximum contrast or sharpness to the image as the optimum sound speed of the subject. The sound speed setter 40 divides the inside of the subject into a plurality of regions, and sets the optimum sound speed for each region.

The controller 42 controls respective components of the ultrasound diagnostic apparatus on the basis of a command input from the operating device 46 by an operator (physician).

The controller 42 gives an instruction to the transmission circuit 16 and the reception circuit 18 so that the piezoelectric element array 14 transmits an intended ultrasonic beam, receives an ultrasonic echo by the ultrasonic beam, and outputs a reception signal.

The storage unit 48 stores an operation program or the like, and a recording medium, such as a hard disk, a flexible disk, an MO, an MT, a RAM, a CD-ROM, a DVD-ROM, an SD card, a CF card, or a USB memory, a server, or the like may be used.

Although the signal processor 20, the DSC 24, the image processor 26, the display controller 28, and the sound speed setter 40 are constituted by a CPU and an operation program which causes the CPU to perform various kinds of processing, these may be constituted by digital circuits.

The operating device 46 is used when the operator performs input operation, and similarly to that for the known ultrasound diagnostic apparatus, has means for instructing freeze (display of a still image) (freeze instruction inputter), switching means of a display mode, such as a B mode or an M mode, adjustment means of image quality (image quality adjustment instruction inputter), setting means of a region of interest (ROI) (region of interest (ROI) setting instruction inputter), and the like.

Figure 2:
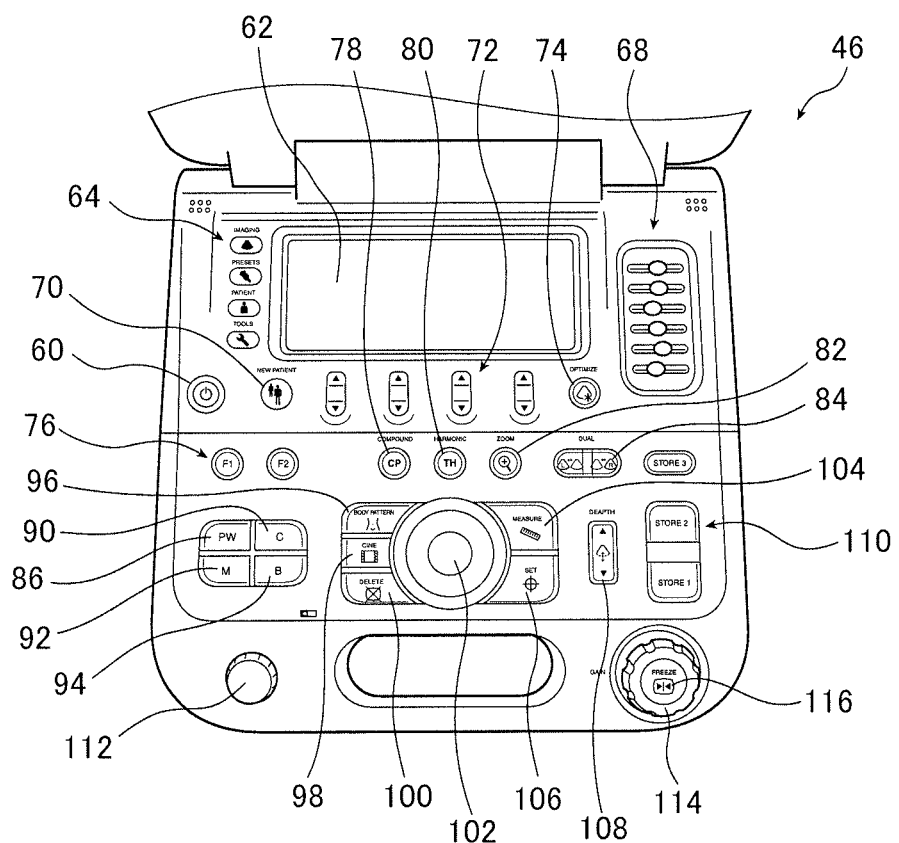
FIG. 2 is a diagram conceptually showing an example of an operating device of the ultrasound diagnostic apparatus shown in FIG. 1.

FIG. 2 conceptually shows an example of the operating device 46 (a part thereof).

In the apparatus of the illustrated example, the operating device 46 is provided with a power switch 60 and a touch panel 62 for performing various kinds of display and input operation.

Reference numeral 64 denotes a menu button.

The menu button 64 is operating means (operating unit) which displays menus for calling various functions on the touch panel 62. In the illustrated example, as an example, four menus of image adjustment, preset, patient information, and system tool are set.

Reference numeral 68 denotes an STC key (attenuation correction key). The STC key 68 is operating means (operating unit) for performing gain adjustment (amplification and attenuation) of each depth of the ultrasound image, that is, luminance adjustment of each depth of the ultrasound image. In the illustrated example, gain adjustment can be performed individually at six depths.

That is, the STC key 68 is an image quality change instruction inputter according to the invention.

Reference numeral 70 denotes a patient information button. The patient information button 70 is operating means (operating unit) for displaying patient information on the display unit 30.

Reference numeral 72 denotes a menu control switch. The menu control switch 72 is used to perform operation of each menu displayed on the touch panel 62 by the menu button 64, and in the illustrated example, four operating means (operating units) are set.

Reference numeral 74 denotes an OPTIMIZE button. The OPTIMIZE button 74 is operating means (operating unit) which enables an automatic attenuation correction and sound speed correction function.

Reference numeral 76 denotes a function button. The function button 76 is operating means (operating unit) in which an examiner can arbitrarily set the function of the button by a system setting function.

Reference numeral 78 denotes a COMPOUND button.

The COMPOUND button 78 is operating means (operating unit) which starts and stops a compound harmonic mode (hereinafter, also referred to as a CH mode) in which an ultrasonic echo having the same center frequency as the transmitted ultrasonic wave (hereinafter, also referred to as a fundamental wave) and an ultrasonic echo of a harmonic of the fundamental wave are received and synthesized, thereby reducing speckle noise.

In the illustrated example, if the COMPOUND button 78 is pressed in a state where display in a different image mode is performed, the image mode is transited to the CH mode. If the COMPOUND button 78 is pressed in a state where display in the CH mode is performed, the image mode is transited to a fundamental image mode (hereinafter, also referred to as a fundamental wave mode) in which an ultrasonic echo having the same center frequency as a fundamental wave is received.

Reference numeral 80 denotes a HARMONICS button. The HARMONICS button 80 is operating means (operating unit) which starts and stops a tissue harmonic mode (hereinafter, also referred to as a THI mode) in which an ultrasonic echo of a harmonic of a fundamental wave is received and an ultrasound image is produced.

In the illustrated example, if the HARMONICS button 80 is pressed in a state where display in a different image mode is performed, the image mode is transited to the THI mode. If the HARMONICS button 80 is pressed in a state where display in the THI mode is performed, the image mode is transited to the fundamental wave mode.

That is, the COMPOUND button 78 and the HARMONICS button 80 are each a mode change instruction inputter according to the invention.

Reference numeral 82 denotes a ZOOM button. The ZOOM button 82 is operating means (operating unit) which starts an enlargement (zooming-in) function of the ultrasound image displayed on the display unit 30.

Reference numeral 84 denotes a dual mode selector switch. The dual mode selector switch 84 is operating means (operating unit) which switches an operable image when ultrasound diagnosis in a dual mode such as a B/C mode is performed.

Reference numerals 86 to 94 denote display mode selection means (display mode switching means). That is, these means are each the mode change instruction inputter of the invention.

Reference numeral 86 denotes a PW button. The PW button 86 is operating means (operating unit) which starts and stops a pulse Doppler mode.

Reference numeral 90 denotes a C button. The C button 90 is operating means (operating unit) which starts and stops a color Doppler mode.

Reference numeral 92 denotes an M button. The M button 92 is operating means (operating unit) which starts and stops an M mode.

Reference numeral 94 denotes a B button. The B button 94 is operating means (operating unit) which starts and stops a B mode.

Reference numeral 96 denotes a BODY PATTERN button. The BODY PATTERN button 96 is operating means (operating unit) which is used to display a body pattern, that is, a graphic pattern representing a site to be imaged.

Reference numeral 98 denotes a CINE button. The CINE button 98 is operating means (operating unit) which is used to replay and stop a motion image clip.

Reference numeral 100 denotes a DELETE button. The DELETE button 100 is operating means (operating unit) which is used to return to a previous process during measurement so as to restart the measurement.

Reference numeral 102 denotes a trackball. The trackball 102 is operating means (operating unit) which is used to perform movement of a cursor, determination of the size or position of a region of interest (ROI), arrangement of a measurement tool, redisplay of a motion image clip, and the like. The trackball 102 constitutes a part of an ROI setting instruction inputter, that is, a part of the observation target range instruction inputter in the invention.

The operating device 46 of the ultrasound diagnostic apparatus of the invention may use a so-called track pad (touch pad), instead of the trackball.

Reference numeral 104 denotes a MEASURE button. The MEASURE button 104 is operating means (operating unit) which starts a dynamic caliper, a calculation menu, or a Doppler waveform autotracing function.

Reference numeral 106 denotes a SET button. The SET button 106 is operating means (operating unit) which is used to select (determine) the item or function on the screen of the display unit 30.

In the ultrasound diagnostic apparatus 10, as an example, the ROI is determined by pressing the SET button 106. That is, the SET button 106 constitutes a part of the observation target range instruction inputter in the invention.

Reference numeral 108 denotes a DEPTH button. The DEPTH button 108 is operating means (operating unit) which is used to change (increase and decrease) the observation depth of the ultrasound image. That is, the DEPTH button 108 is an observation target range instruction inputter according to the invention.

Reference numeral 110 denotes a STORE button. The STORE button 110 is operating means (operating unit) which is used to store an image displayed on the display unit 30 in a device set in advance or print the image.

Reference numeral 112 denotes an encoder dial. The encoder dial 112 is operating means (operating unit) which is used to adjust a Doppler angle in the pulse Doppler mode or to rotate the mark of the probe at the time of body pattern display.

Reference numeral 114 denotes a GAIN dial. The GAIN dial 114 is operating means (operating unit) which is used to adjust a gain (luminance of an ultrasound image) in the B mode, the M mode, the color Doppler mode, and the pulse Doppler mode. That is, the GAIN dial 114 is an image quality change instruction inputter according to the invention.

Reference numeral 116 denotes a FREEZE button (freeze switch). The FREEZE button 116 is operating means (operating unit) which is used to switch between a live mode, in which a motion image (live image) of an ultrasound image is displayed at a predetermined frame rate, and a freeze mode, in which a still image (freeze image) of an ultrasound image is displayed. That is, the FREEZE button 116 is the freeze instruction inputter of the invention which instructs display of a still image (freeze image).

In the illustrated example, the FREEZE button 116 is arranged in the center of the GAIN dial 114.

Hereinafter, the invention will be described in more detail while describing the action of the ultrasound diagnostic apparatus 10. The recording medium of the invention is a computer-readable recording medium having recorded thereon a program which causes a computer to execute a method of producing an ultrasound image described below.

As described above, in the ultrasound diagnostic apparatus 10, as an example, the sound speed (optimum sound speed) of the ultrasonic wave in the subject is updated (reset) once for every predetermined number of frames.

In addition, in the ultrasound diagnostic apparatus 10, when an instruction of freeze is given by the above-described FREEZE button 116, when an instruction of ROI setting is given using the trackball 102 or the like, when an instruction to change an observation depth is given by the DEPTH button 108, when an instruction to change a gain is given by the STC key 68 or the GAIN dial 114, and when an instruction to change an image mode is given by the COMPOUND button 78 or the HARMONICS button 80 (further, by the B button 94 or the like), the optimum sound speed is updated.

In the ultrasound diagnostic apparatus 10, the subject (an ultrasound image to be produced) is divided into a plurality of regions, and the optimum sound speed is updated (set) for each region.

The update of the optimum sound speed is performed by transmission and reception of an ultrasonic wave for sound speed setting ("transmission and reception of an ultrasonic wave" being hereafter also referred to as "ultrasonic transmission and reception" or simply as "transmission and reception"). The transmission and reception for sound speed setting is transmission and reception in which a transmission focus for sound speed setting is formed by forming a transmission focus with higher density than transmission and reception for producing a B-mode image in one scan line (sound ray signal to be produced, namely, ultrasonic beam to be produced).

Figure 3A:
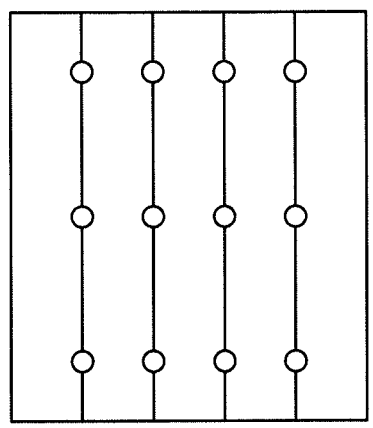
FIGS. 3A and 3B are conceptual diagrams illustrating transmission and reception of ultrasonic waves in the ultrasound diagnostic apparatus shown in FIG. 1.

FIG. 3A conceptually shows transmission and reception for producing a B-mode image (hereinafter, also referred to as normal transmission and reception), and FIG. 3B conceptually shows transmission and reception for sound speed setting.

Figure 3B:
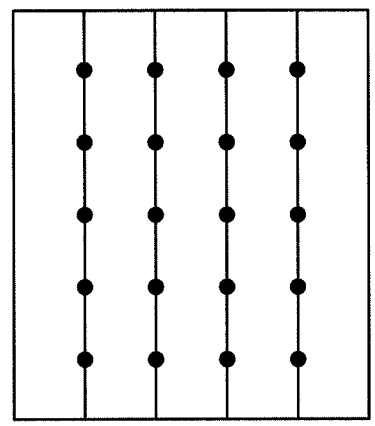

In FIGS. 3A and 3B, the vertical direction is a depth direction (the transmission and reception direction of the ultrasonic wave), and the upper side in the drawing is a shallower side (piezoelectric element array 14 side). The horizontal direction is an azimuth direction (the arrangement direction of the piezoelectric elements in the piezoelectric element array 14).

In FIGS. 3A and 3B, a solid line which extends in the depth direction is a scan line. The position in the azimuth direction of each scan line in the normal transmission and reception of FIG. 3A and the position in the azimuth direction of each scan line in the transmission and reception for sound speed setting of FIG. 3B coincide with each other.

In FIG. 3A, a white circle on the scan line is the transmission focus in the normal transmission and reception. Meanwhile, in FIG. 3B, a black circle on the scan line is the transmission focus for sound speed setting (hereinafter, also referred to as a focus for setting).

As shown in FIG. 3, in this example, in the normal transmission and reception, three transmission focuses (three positions of the transmission focus in the depth direction) are defined for one scan line. That is, in the normal transmission and reception, three transmissions and receptions having different transmission focuses are performed for one scan line.

In contrast, in the transmission and reception for sound speed setting, five transmission focuses, that is, five focuses for setting are defined for one scan line. That is, in the transmission and reception for sound speed setting, five transmissions and receptions having different transmission focuses are performed for one scan line.

The regions in which the optimum sound speed is set are set by dividing the subject parallel to the azimuth direction and the depth direction into the form of a lattice, with each region centering at the focus for setting.

That is, the optimum sound speed is set correspondingly to each focus for setting.

In the ultrasound diagnostic apparatus 10 of the invention, the regions of the subject, that is, the focuses for setting in the transmission and reception for sound speed setting may be appropriately set in accordance with required image quality, the frame rate of an ultrasound image to be displayed, the arithmetic capacity (processing speed) of the ultrasound diagnostic apparatus 10, or the like.

Preferably, the focus for setting is produced at the identical positions corresponding to all pixels of an ultrasound image to be produced. Alternatively, one transmission focus may be set for every number of pixels set appropriately, for example, one for every three pixels of an ultrasound image, one for every nine pixels thereof, or the like. Alternatively, an ultrasound image may be divided into a specified number of equal regions, for example, 10 or 20 equal regions, with the number being appropriately specified.

Further, the number of regions, the number of focuses for setting on one scan line, and the like may be set by the operator. The number of regions, the number of focuses for setting, and the like may be set by mode selection or the like.

In the invention, the focus for setting may not necessarily be formed correspondingly to all regions. For example, a region including no focus for setting may be set, and in regard to this region, the optimum sound speed may be set by interpolation using the optimum sound speed set in a region including a focus for setting.

In the normal transmission and reception and the transmission and reception for sound speed setting, the number of scan lines in one frame and the number of focuses on one scan line are not limited to the example shown in FIGS. 3A and 3B. For example, in the normal transmission and reception, one scan line may be formed with one transmission focus (single transmission and reception), instead of three transmission focuses (three transmissions and receptions). That is, in the invention, in the normal transmission and reception and the transmission and reception for sound speed setting, any number of transmission focuses per scan line will do as long as the transmission and reception for sound speed setting is higher in number of transmission focuses (number of times of transmission and reception) per scan line.

Further, although the transmission and reception for sound speed setting only has a larger number of transmission focuses on one scan line than the normal transmission and reception in the example shown in FIGS. 3A and 3B, the transmission and reception for sound speed setting may have a larger number of scan lines than the normal transmission and reception as necessary.

As described above, in the transmission and reception for sound speed setting, five transmissions and receptions of an ultrasonic wave are performed so that five focuses for setting are formed on one scan line. When updating the optimum sound speed, the controller 42 gives an instruction to the transmission circuit 16 and the reception circuit 18 so that the piezoelectric element array 14 transmits an ultrasonic beam which forms an intended transmission focus, and receives an ultrasonic echo by the ultrasonic beam.

The reception signals output from the respective piezoelectric elements of the piezoelectric element array 14 by the transmission and reception for sound speed setting are subjected to amplification and A/D conversion by the reception circuit 18 to produce reception data, and reception data is sequentially stored in the reception data memory 36.

When reception data by the transmission and reception for sound speed setting is stored in the reception data memory 36, the sound speed setter 40 supplies a first set sound speed S1 to the signal processor 20.

The signal processor 20 reads reception data by the transmission and reception for sound speed setting from the reception data memory 36, and performs delay correction on reception data on the basis of the supplied set sound speed S1 to produce delay data. In addition, the signal processor 20 performs the reception focusing processing by adding the produced delay data to produce a sound ray signal. Further, the signal processor 20 performs attenuation correction and envelope detection processing on the sound ray signal to produce a B-mode image signal based on the first set sound speed S1.

The B-mode image signal is raster-converted in the DSC 24, is subjected to various kinds of image processing in the image processor 26, and is then stored in the image memory 32 as a B-mode image signal for sound speed setting based on the first set sound speed S1.

If the B-mode image signal corresponding to the first set sound speed S1 given from the sound speed setter 40 is stored in the image memory 32, the sound speed setter 40 supplies a second set sound speed S2, the value of which changes from the first set sound speed S1 by a predetermined amount, to the signal processor 20. Thereafter, a B-mode image for sound speed setting based on the second set sound speed S2 is formed and stored in the image memory 32 in a similar way as described above.

In this way, a plurality of set sound speeds S1 to Sn are sequentially given from the sound speed setter 40 to the signal processor 20, and the B-mode image signals based on the set sound speeds S1 to Sn are produced by the ultrasound image producer 50 and stored in the image memory 32 as B-mode image signals for sound speed setting.

If the B-mode image signals, which are produced by the transmission and reception for sound speed setting and are based on the set sound speeds S1 to Sn, are stored in the image memory 32, the sound speed setter 40 analyzes each B-mode image signal. Using the analysis result, the sound speed setter 40 sets a sound speed which gives maximum image contrast or sharpness to the image as an optimum sound speed of the subject from the set sound speeds S1 to Sn, and supplies the optimum sound speed to the signal processor 20.

The signal processor 20 to which the newly set optimum sound speed is supplied updates the optimum sound speed to the newly supplied optimum sound speed.

The analysis of the B-mode image signal and the setting of the optimum sound speed are performed for each region, that is, for each focus for setting. That is, the sound speed which gives maximum image contrast or sharpness to the image is selected for each region and set as the optimum sound speed of each region.

That is, the optimum sound speed is a sound speed inside the subject between the region and the piezoelectric element on the supposition that the subject from the region to the piezoelectric element is uniform. In other words, the optimum sound speed is an average sound speed inside the subject from the region to the piezoelectric element.

A method of setting a sound speed in the subject is not limited to this method, and various known sound speed setting methods which are executed by the conventional ultrasound diagnostic apparatus or ultrasound image production method can be used.

Meanwhile, in the ultrasound diagnostic apparatus 10, in the normal transmission and reception, as conceptually shown in FIG. 3A, three transmissions and receptions having different transmission focuses are performed for one scan line. The controller 42 gives an instruction to the transmission circuit 16 and the reception circuit 18 so that the piezoelectric element array 14 transmits an ultrasonic beam which forms an intended transmission focus and receives an ultrasonic echo by the ultrasonic beam.

The reception signals output from the respective piezoelectric elements of the piezoelectric element array 14 by the normal transmission and reception are subjected to amplification and A/D conversion in the reception circuit 18 to produce reception data, and reception data is sequentially stored in the reception data memory 36.

If reception data is stored in the reception data memory 36, the signal processor 20 reads reception data and performs delay correction on the basis of the optimum sound speed set ahead to produce delay data. Then, the signal processor 20 performs reception focusing processing by adding the produced delay data to produce a sound ray signal. Further, the signal processor 20 performs attenuation correction and envelope detection processing on the sound ray signal to produce a B-mode image signal. Alternatively, reception data may be supplied directly from the reception circuit 18 to the signal processor 20.

The B-mode image signal is raster-converted in the DSC 24, is subjected to various kinds of image processing in the image processor 26, and is then stored in the image memory 32 as a B-mode image signal.

The B-mode image signal processed by the image processor 26 is sent to the display controller 28, and the B-mode image, information of the subject, or the like is displayed on the display unit 30.

In the live mode, the normal transmission and reception shown in FIG. 3A is performed repeatedly in accordance with a predetermined frame rate, the above-described processing is sequentially performed on the reception signal output from the piezoelectric element array 14, and a motion image of the B-mode image is displayed at the predetermined frame rate.

Here, in the ultrasound diagnostic apparatus 10, it is assumed that in a state where the normal transmission and reception shown in FIG. 3A is performed at a predetermined frame rate, and a motion image in the live mode is displayed, the FREEZE button 116 is operated, and freeze is instructed (display of a still image is instructed (that is, switching to the freeze mode is instructed)). If freeze is instructed, the controller 42 gives an instruction to the transmission circuit 16 and the reception circuit 18 so that the piezoelectric element array 14 performs the transmission and reception for sound speed setting shown in FIG. 3B in transmission and reception immediately after freeze is instructed, and as described above, the sound speed setter 40 sets the optimum sound speed and updates the optimum sound speed.

Figure 4:
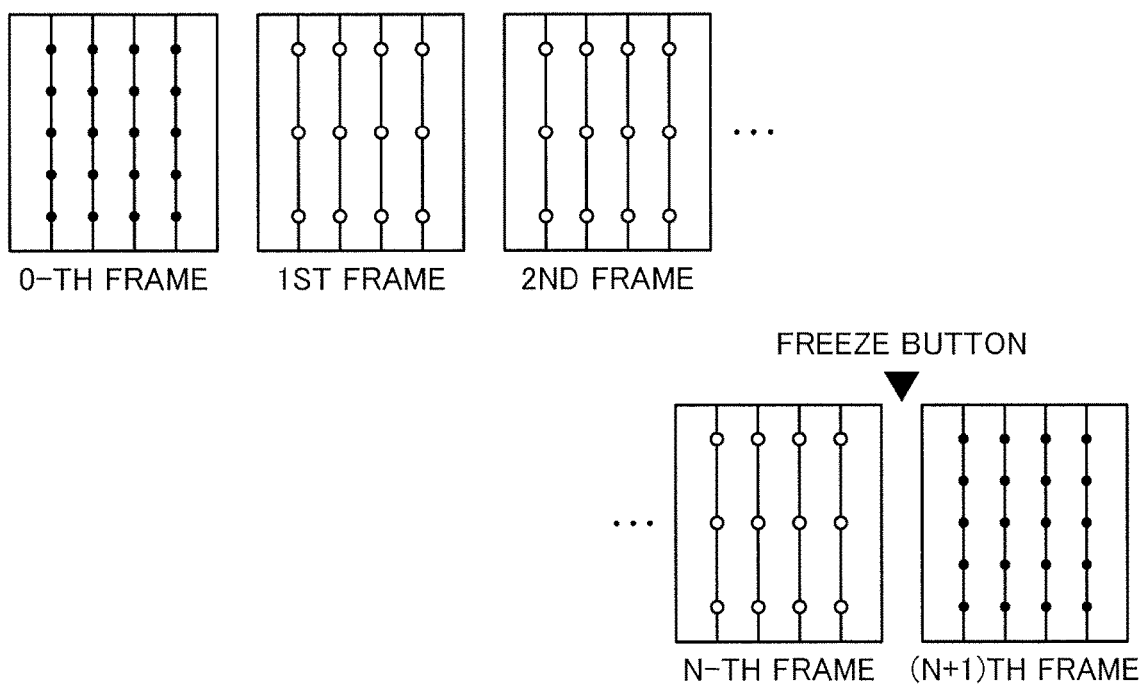
FIG. 4 is a conceptual diagram illustrating an example of update of a sound speed in the ultrasound diagnostic apparatus shown in FIG. 1.

As conceptually shown in FIG. 4, when a frame in which the sound speed is last updated (set) is a zero-th frame, if the FREEZE button 116 is operated in the N-th frame and freeze is instructed, the transmission and reception for sound speed setting shown in FIG. 3B is performed in the (N+1)th frame which is a frame immediately after the instruction of freeze.

In the invention, the transmission and reception for sound speed setting may be performed in a frame after the frame immediately after the instruction of freeze or the instruction described below such as an instruction of an observation target range, an instruction to change image quality, an instruction to change an image mode, or the like is performed. That is, the transmission and reception for sound speed setting may be performed not in the (N+1)th frame, but in the (N+2)th frame or a frame after the (N+2)th frame.

However, it is preferable that the transmission and reception for sound speed setting be performed in the frame ((N+1)th frame) immediately after the instruction of freeze or the instruction described below such as an instruction of an observation target range, an instruction to change image quality, an instruction to change an image mode, or the like is performed. Accordingly, the update of the sound speed can rapidly be performed in response to various instructions (operations), whereby the enhancement of the quality of an ultrasound image desired by the operator can be performed more rapidly.

In particular, in regard to the instruction of freeze, the operator wants to see a still image at time point when freeze is performed. For this reason, it is preferable that, after freeze is instructed, the transmission and reception for sound speed setting be performed in a frame immediately after the freeze instruction by the FREEZE button 116.

After the transmission and reception for sound speed setting is performed in the (N+1)th frame, as described above, reception data thereof is stored in the reception data memory 36, the signal processor 20 reads reception data from the reception data memory 36, and the optimum sound speed is set by the sound speed setter 40.

The sound speed setter 40 supplies the newly set optimum sound speed to the signal processor 20, and the signal processor 20 updates the optimum sound speed. That is, in the ultrasound diagnostic apparatus 10, as a preferred embodiment, the transmission and reception for sound speed setting is performed immediately after freeze is instructed, and the optimum sound speed is updated.

After the optimum sound speed is updated, the signal processor 20 reads reception data by the transmission and reception for sound speed setting in the (N+1)th frame from the reception data memory 36 again, and performs delay correction on the basis of the updated optimum sound speed to produce a B-mode image signal. When producing the B-mode image signal, thinning or the like of reception data may be performed as necessary.

The B-mode image signal in the (N+1)th frame produced by the signal processor 20 is processed by the DSC 24 and the image processor 26, and is displayed on the display unit 30 as a still image according to the freeze instruction.

As described above, according to the invention, in the ultrasound diagnostic apparatus, a still image according to the instruction of freeze is produced and displayed by performing the transmission and reception for sound speed setting immediately after the instruction of freeze to update the sound speed and producing an ultrasound image on the basis of the updated sound speed.

Therefore, according to the invention, it is possible to produce a still image according to the instruction of freeze at an accurate sound speed, and to make a still image of an ultrasound image desired to be observed in detail a high-quality ultrasound image with no image quality deterioration due to distortion or the like.

In the invention, the B-mode image may be produced using reception data obtained by the normal transmission and reception in the N-th frame in which freeze is instructed.

In this case, reception data by at least the most recent normal transmission and reception is constantly stored in the reception data memory 36.

In the ultrasound diagnostic apparatus 10, as shown in FIG. 4, in a state where the normal transmission and reception shown in FIG. 3A is repeatedly performed at a predetermined frame rate, and a motion image in the live mode is displayed, if freeze is instructed in the N-th frame by the FREEZE button 116, as described above, the transmission and reception for sound speed setting is performed in the subsequent (N+1)th frame to update the optimum sound speed.

After the optimum sound speed is updated, the signal processor 20 reads reception data in the N-th frame from the reception data memory 36 and performs delay correction on the basis of the updated optimum sound speed to produce B-mode image data, B-mode image data is processed in the DSC 24 and the image processor 26, and a B-mode image by the transmission and reception in the N-th frame is displayed on the display unit 30 as a still image according to the freeze instruction.

Alternatively, as the still image according to the freeze instruction, the B-mode image obtained by the normal transmission and reception in the N-th frame and the B-mode image obtained by the transmission and reception for sound speed setting in the (N+1)th frame may be displayed in parallel. Further, selection means (selection instruction inputter) may be provided using the trackball 102 or the like, and only a selected one out of the two B-mode images displayed in parallel may be displayed.

Any one of the display of only the B-mode image in the N-th frame, the display of the B-mode image in the N-th frame and the B-mode image in the (N+1)th frame, and the display of only the B-mode image in the (N+1)th frame may be selected by the mode or the like.

According to this embodiment, the operator can observe the B-mode image when freeze is instructed by the FREEZE button 116, thereby it is possible to perform diagnosis or the like. Further, the B-mode image when freeze is instructed can be compared with the B-mode image immediately after the freeze, thereby it is possible to perform observation, diagnosis, or image selection.

In the invention, reception data in the first to N-th frames as well as reception data in the N-th frame or in the N-th and (N+1)th frames may be stored in the reception data memory 36, reception data in the first to N-th frames may be processed on the basis of the updated optimum sound speed to produce B-mode images, and the B-mode images may be displayed on the display unit 30 in parallel. Further, selection means (selection instruction inputter) may be provided in the operating device 46, one or more images from the B-mode images displayed in parallel may be selected, and only the selected image or images may be displayed.

Otherwise, reception data in the (N−n)th (where n is an integer less than N) to N-th frames may be stored, and the same processing may be performed thereon. Furthermore, n may be selected by the operator.

In the invention, the B-mode images based on both of the optimum sound speed before update used in the frames before the (N+1)th frame and the optimum sound speed updated by the transmission and reception for sound speed setting in the (N+1)th frame may be displayed.

In this embodiment, reception data obtained by the transmission and reception in all the frames immediately after the optimum sound speed is last updated, from the first one to the N-th one, is stored in the reception data memory 36.

In the ultrasound diagnostic apparatus 10, similarly to the above, as shown in FIG. 4, in a state where the normal transmission and reception shown in FIG. 3A is repeatedly performed at a predetermined frame rate, and a motion image in the live mode is displayed, if freeze is instructed in the N-th frame by the FREEZE button 116, as described above, the transmission and reception for sound speed setting is performed in the subsequent (N+1)th frame to update the optimum sound speed. In addition, the optimum sound speed before update, that is, the optimum sound speed which is updated in the zero-th frame and is used until the N-th frame is stored in the signal processor 20.

After the optimum sound speed is updated, the signal processor 20 reads reception data in the first to N-th frames from the reception data memory 36, and produces a B-mode image signal subjected to delay correction on the basis of the updated optimum sound speed and a B-mode image signal subjected to delay correction on the basis of the optimum sound speed before update for each frame, and similarly to the above, the B-mode image signals are processed by the DSC 24 and the image processor 26.

Subsequently, the B-mode images of the first to N-th frames based on the updated optimum sound speed and the B-mode images of the first to N-th frames based on the optimum sound speed before update, both processed by the image processor 26, are displayed on the display unit 30 in parallel.

Alternatively, selection means (selection instruction inputter) may be provided in the operating device 46, and out of the B-mode images displayed in parallel, either the B-mode images based on the updated optimum sound speed or the B-mode images based on the optimum sound speed before update as selected may solely be displayed. Further, one or more B-mode images out of the B-mode images displayed in parallel may be selected, and only the selected B-mode image or images may be displayed.

In addition to these B-mode images, B-mode image produced by the transmission and reception for sound speed setting in the (N+1)th frame may be displayed.

According to this embodiment, for performing diagnosis or the like, the operator can compare and observe the B-mode images which are observed until freeze is instructed and the B-mode images based on the optimum sound speed immediately after freeze is instructed. It is preferable that the B-mode images as observed until freeze is instructed and the B-mode images based on the optimum sound speed immediately after freeze is instructed are compared by the operator and preferred image or images are displayed.

Also in this embodiment, reception data in the (N−n)th (where n is an integer less than N) to N-th frames, instead of the first to N-th frames, may be stored, and the same processing as described above may be performed. Furthermore, n may be selected by the operator.

In this embodiment, the B-mode image based on the optimum sound speed before update may be stored, for example, in the image memory 32 or the like, and the image may be read therefrom and displayed.

Further, in the invention, one or more out of three display methods, namely, the display of the B-mode image in the (N+1)th frame based on the updated optimum sound speed, the display of the B-mode image in the N-th frame (and the B-mode image in the (N+1)th frame) based on the updated optimum sound speed, and the display of the B-mode image based on the updated optimum sound speed and the B-mode image based on the optimum sound speed before update, may be selected by mode selection or the like.

As another embodiment, the FREEZE button 116 may be configured such that it can be long pressed, and a still image may be displayed in accordance with this operation of the FREEZE button 116.

In the ultrasound diagnostic apparatus 10, as conceptually shown in FIG. 5, in a state where the normal transmission and reception shown in FIG. 3A is performed at a predetermined frame rate, and a motion image in the live mode is displayed, if freeze is instructed by the FREEZE button 116 (FREEZE button ON), subsequently, the piezoelectric element array 14 performs the transmission and reception for sound speed setting shown in FIG. 3B at a predetermined frame rate as conceptually shown in FIG. 4.

The frame rate of the transmission and reception for sound speed setting at this time may be different from the frame rate of the normal transmission and reception.

While the FREEZE button 116 is ON, the transmission and reception for sound speed setting is repeatedly performed, and reception data is sequentially stored in the reception data memory 36.

In the sound speed setter 40, the optimum sound speed is set correspondingly to all frames, in which the transmission and reception for sound speed setting is performed, in the similar way as described above and the set optimum sound speeds are supplied to the signal processor 20. The signal processor 20 reads reception data from the reception data memory 36, and performs delay correction based on the corresponding optimum sound speed to produce a B-mode image signal. The B-mode image signal is processed by the DSC 24 and the image processor 26, and a motion image of the B-mode image by the transmission and reception for sound speed setting is displayed on the display unit 30 at a predetermined frame rate.

Figure 5:
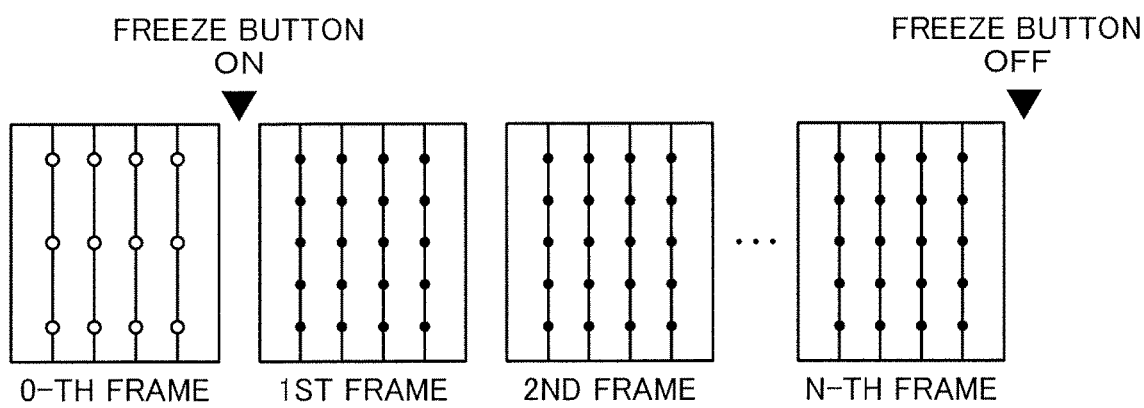
FIG. 5 is a conceptual diagram illustrating another example of update of a sound speed in the ultrasound diagnostic apparatus shown in FIG. 1.

From this state, as shown in FIG. 5, if the FREEZE button 116 is released (FREEZE button OFF), the B-mode image in the frame (N-th frame) immediately before the release of the FREEZE button is displayed on the display unit 30 as a still image according to the freeze instruction. Alternatively, still images of the B-mode images for n frames (where n is an integer less than N) before the N-th frame may be displayed on the display unit 30.

That is, according to this embodiment, it is possible to display the B-mode image based on the sound speed at time point when freeze is instructed.

In addition, in the ultrasound diagnostic apparatus 10 of the illustrated example, in a state where the normal transmission and reception shown in FIG. 3A is repeatedly performed in accordance with a predetermined frame rate, and the B-mode image in the live mode is displayed, also when the instruction on an observation target range is given by operation of the operating device 46, the transmission and reception for sound speed setting is performed in response to this instruction, and the optimum sound speed is updated.

Specifically, in the ultrasound diagnostic apparatus 10, it is assumed that the normal transmission and reception shown in FIG. 3A is performed at a predetermined frame rate as described above, and the DEPTH button 108 is operated during the B-mode image is displayed. In response to this operation, that is, the instruction to change the observation depth (depth of visual field), the controller 42 gives an instruction to the transmission circuit 16 and the reception circuit 18 so that the piezoelectric element array 14 performs the transmission and reception for sound speed setting in the transmission and reception immediately after the instruction to change the observation depth, and the sound speed setter 40 sets the optimum sound speed and updates the optimum sound speed in a similar way as described above.

As an example, the DEPTH button 108 is a so-called neutral-off locker switch (seesaw switch), and performs operation (gives an instruction) to increase and decrease the observation depth.

In the illustrated example, an end portion on a deep side of the ultrasound image is moved in the depth direction to increase or decrease the observation depth. However, in the invention, alternatively, an end portion on a shallow side of the ultrasound image may be moved in the depth direction to increase or decrease the observation depth, or the increase or decrease by movement of the end portion on the shallow side and movement of the end portion on the deep side may be selected.

In the invention, change means (change instruction inputter) for the observation depth is not limited thereto, and means for changing only the observation depth without changing the extent of the observation region (the extent of the observation field) in the depth direction may be provided. Alternatively, both means for increasing or decreasing the observation depth and means for changing only the observation depth without changing the extent of the observation region may be provided.

Figure 6A:
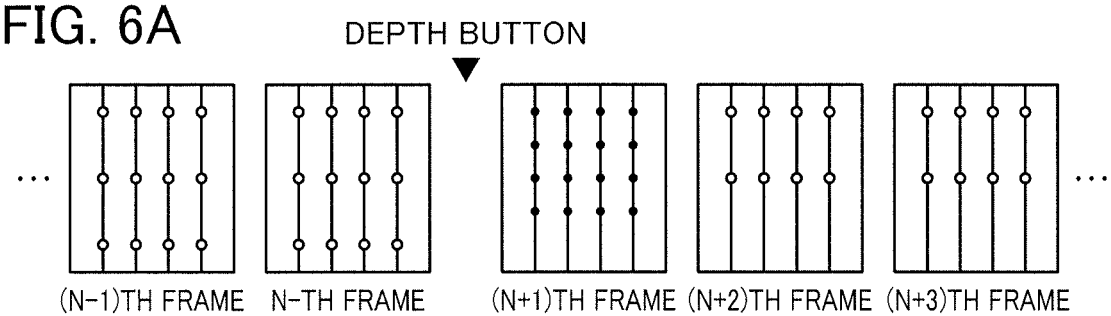
FIGS. 6A and 6B are conceptual diagrams illustrating another example of update of a sound speed in the ultrasound diagnostic apparatus shown in FIG. 1.

In the ultrasound diagnostic apparatus 10, as conceptually shown in FIG. 6A, when the normal transmission and reception shown in FIG. 3A is performed at a predetermined frame rate, if an instruction to decrease the observation depth is given in the N-th frame by the DEPTH button 108, the transmission and reception for sound speed setting is performed in the next (N+1)th frame in response to this instruction.

Figure 6B:
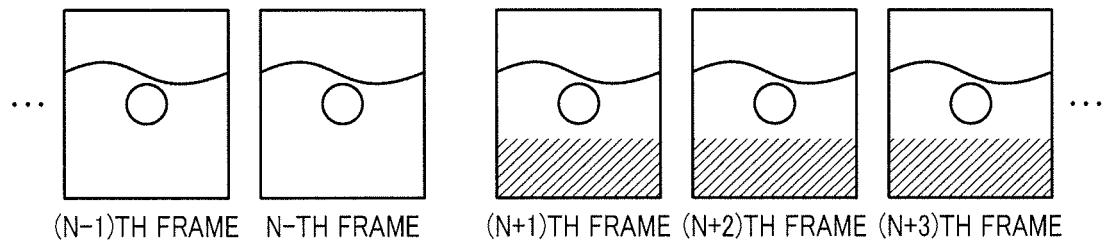

FIG. 6B conceptually shows ultrasound images which are produced by transmission and reception of an ultrasonic wave in individual frames.

When the instruction to decrease the observation depth is given by the DEPTH button 108, as transmission and reception for sound speed setting, the transmission and reception shown in FIG. 3B which forms five focuses for setting for one scan line may be performed. However, when the decrease of the observation depth is performed (an instruction to make the end portion on the deep side shallower is given), an ultrasonic echo is not received from a reduced deep region, and an ultrasound image is not produced. Accordingly, it is purposeless to obtain the optimum sound speed in this region, and transmission and reception which forms a focus for setting in this region is not required.

For this reason, when the observation depth is decreased, as shown in the (N+1)th frame of FIG. 6A, it is preferable that transmission and reception which forms a focus for setting at the deepest position on each scan line in the transmission and reception for sound speed setting is not performed. That is, in this example, the transmission and reception for sound speed setting is performed four times for each scan line in accordance with the decrease of the observation depth.

After the transmission and reception for sound speed setting is performed in the (N+1)th frame, as described above, reception data thereof is stored in the reception data memory 36, the signal processor 20 reads reception data from the reception data memory 36, and the optimum sound speed is set by the sound speed setter 40.

The sound speed setter 40 supplies the newly set optimum sound speed to the signal processor 20, and the signal processor 20 updates the optimum sound speed. That is, in the ultrasound diagnostic apparatus 10, as a preferred embodiment, immediately after the instruction to decrease the observation depth is performed by the DEPTH button 108, the transmission and reception for sound speed setting is performed, and the optimum sound speed is updated.

After the optimum sound speed is updated, the signal processor 20 reads reception data by the transmission and reception for sound speed setting in the (N+1)th frame from the reception data memory 36 again, performs delay correction on the basis of the updated optimum sound speed, and thereafter, as described above, a B-mode image signal is produced. When producing the B-mode image signal, thinning or the like of reception data may be performed as necessary.

Similarly to the above, the B-mode image signal in the (N+1)th frame produced by the signal processor 20 is processed by the DSC 24 and the image processor 26, and is displayed on the display unit 30.

In the transmission and reception for sound speed setting in the (N+1)th frame, the B-mode image may not be produced, but only the setting of the optimum sound speed may be performed. In this regard, the same applies to different transmission and reception for sound speed setting.

After the transmission and reception for sound speed setting in the (N+1)th frame ends, the controller 42 gives an instruction to the transmission circuit 16 and the reception circuit 18 so that the piezoelectric element array 14 performs the normal transmission and reception for producing a B-mode image with a decreased observation depth in the (N+2)th frame and afterward.

Here, the transmission and reception after the observation depth is decreased may be the normal transmission and reception shown in FIG. 3A. However, as described above, when the decrease of the observation depth is performed, an ultrasound image is not produced for a reduced deep region, and the transmission and reception which forms a transmission focus in this region is purposeless.

For this reason, when the observation depth is decreased, it is preferable that in the normal transmission and reception, the transmission and reception which forms a focus for setting at the deepest position on each scan line is not performed, as shown in the (N+2)th frame and afterward in FIG. 6A. That is, in this example, in the normal transmission and reception, two transmissions and receptions are performed for each scan line in accordance with the decrease of the observation depth.

Similarly to the above, a reception signal by the normal transmission and reception in the (N+2)th frame is processed into reception data and as such stored in the reception data memory 36. The signal processor 20 reads reception data, performs delay correction on the basis of the updated optimum sound speed to produce a B-mode image signal, and displays a B-mode image on the display unit 30. As conceptually shown in FIG. 6B, the B-mode image becomes an image having a decreased observation depth with no luminance in a deeper portion.

In the (N+3)th frame and afterward, the same normal transmission and reception and the production and display of the B-mode image are repeatedly performed. In the case where the observation depth is decreased, the frame rate is shortened in accordance with the decreased observation depth.

When the update of the optimum sound speed in the (N+1)th frame is too late, the B-mode image may be produced on the basis of the optimum sound speed used before the (N+1)th frame. In this regard, the same applies to the update of the optimum sound speed in response to an instruction on a different observation target range (and an instruction to change image quality and an instruction to change an image mode described later).

In the ultrasound diagnostic apparatus 10, also in the case where the increase of the observation depth is instructed by the DEPTH button 108 in a state where the observation depth is decreased as shown in FIGS. 6A and 6B, similarly, the transmission and reception for sound speed setting is performed and the optimum sound speed is updated.

Figure 7A:
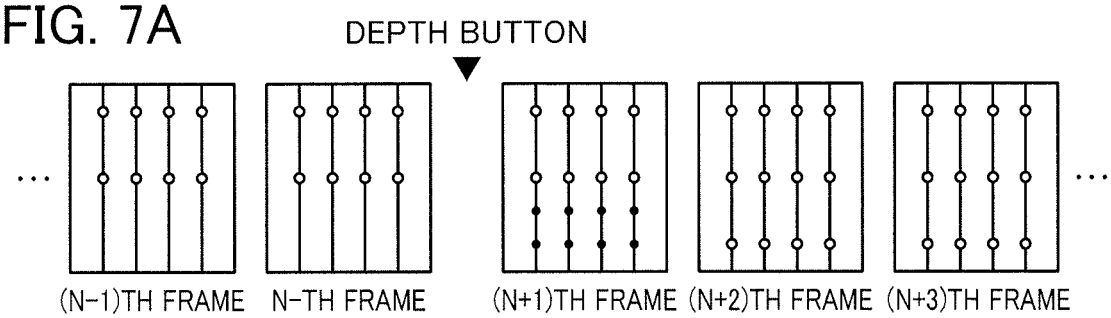
FIGS. 7A and 7B are conceptual diagrams illustrating another example of update of a sound speed in the ultrasound diagnostic apparatus shown in FIG. 1.
Figure 7B:
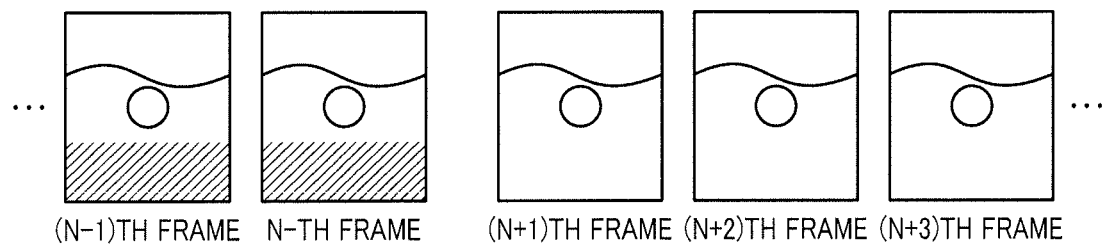

That is, as conceptually shown in FIGS. 7A and 7B, in a state where the ultrasound image having a decreased observation depth is produced and displayed by the normal transmission and reception according to a decreased observation depth, if an instruction to increase the observation depth (in this example, an instruction to restore the observation depth) is given in the N-th frame by the DEPTH button 108, in response to this instruction, the transmission and reception for sound speed setting is performed in the next (N+1)th frame.

Since the optimum sound speed is updated ahead in a depth region under observation, the transmission and reception for sound speed setting when increasing the observation depth is a transmission and reception which forms a focus for setting only in the extended depth region, as shown in FIG. 7A. That is, in this example, four transmissions and receptions in total including two transmissions and receptions which form a focus for setting and two transmissions and receptions which form a transmission focus for B mode forming are performed for one scan line.

However, when increasing the observation depth, the transmission and reception for sound speed setting of FIG. 3B for the formation of focuses for setting corresponding to the entire surface of the ultrasound image may be performed. Further, when the transmission and reception for sound speed setting is performed, the optimum sound speed may be updated over the entire surface in the same way as described above.

After the transmission and reception for sound speed setting is performed in the (N+1)th frame, similarly to the above, reception data is stored in the reception data memory 36, the signal processor 20 reads reception data from the reception data memory 36, and the optimum sound speed is set by the sound speed setter 40.

The sound speed setter 40 supplies the newly set optimum sound speed to the signal processor 20, and the signal processor 20 updates the optimum sound speed. That is, in the ultrasound diagnostic apparatus 10, the transmission and reception for sound speed setting is performed immediately after the increase or decrease of the observation depth is performed by the DEPTH button, and the optimum sound speed is updated.

After the optimum sound speed is updated, the signal processor 20 reads reception data by the transmission and reception for sound speed setting in the (N+1)th frame from the reception data memory 36 again, and performs delay correction on the basis of the updated optimum sound speed to produce a B-mode image signal. When producing the B-mode image signal, thinning or the like of reception data may be performed as necessary.

The B-mode image signal in the (N+1)th frame produced by the signal processor 20 is processed by the DSC 24 and the image processor 26, and is displayed on the display unit 30.

After the transmission and reception for sound speed setting in the (N+1)th frame ends, the controller 42 gives an instruction to the transmission circuit 16 and the reception circuit 18 so that the piezoelectric element array 14 performs the normal transmission and reception shown in FIG. 3A for producing a B-mode image having an increased observation depth.

In response to this instruction, as shown in FIG. 7A, in the (N+2)th frame and afterward, the normal transmission and reception shown in FIG. 3A is repeatedly performed at a predetermined frame rate, and delay correction is performed on reception data obtained by the transmission and reception on the basis of the updated optimum sound speed to produce a B-mode image signal, and as shown in FIG. 7B, a B-mode image having an extended depth region is displayed at a predetermined frame rate.

If the observation depth is increased or decreased as described above, the reception time of the ultrasonic echo changes with the change of the observation depth, and the frame rate also changes, accordingly.

In response to this, as described above, the frequency of the update of the optimum sound speed which is performed regularly, for example, once for every predetermined number of frames may be changed.

In the ultrasound diagnostic apparatus 10 of the illustrated example, also in the case where ROI setting is instructed as the instruction on an observation target range, the update of the optimum sound speed is performed.

As an example, in the ultrasound diagnostic apparatus 10, in a state where a frame representing an ROI (a so-called ROI box) is not displayed, if the ZOOM button 82 is pressed, the ROI box is displayed in the ultrasound image. Subsequently, the position of the ROI box is adjusted by the trackball 102, and the SET button 106 is pressed, whereby the position of the ROI box is determined. Thereafter, the size of the ROI box can be adjusted by operation of the trackball 102, and the SET button 106 is pressed to determine the ROI.

It is possible to return to operation at a previous stage by pressing the DELETE button 100 during operation.

In the ultrasound diagnostic apparatus 10, as shown on the left side of FIGS. 8A and 8B, in a state where the normal transmission and reception shown in FIG. 3A is performed and the B-mode image is displayed, as described above, the display of the frame representing the ROI and the adjustment of the position and size of the ROI are performed, and then, the ROI is determined by the SET button 106.

In FIGS. 8A, 8B, and FIGS. 9A to 9C described later, reference character R denotes the frame representing the ROI.

In response to this instruction to determine an ROI (that is, an instruction to set an ROI), the controller 42 gives an instruction to the transmission circuit 16 and the reception circuit 18 so that the piezoelectric element array 14 performs the transmission and reception for sound speed setting in a frame immediately after the determination instruction. That is, in the ultrasound diagnostic apparatus 10, as a preferred embodiment, the transmission and reception for sound speed setting is performed immediately after the ROI is set by the determination instruction, and the optimum sound speed is updated.

Here, in this transmission and reception, the transmission and reception for sound speed setting of FIG. 3B for the formation of focuses for setting over the entire ultrasound image may be performed. However, preferably, as shown in FIG. 8B, transmission and reception in which a focus for setting is formed only in the ROI box, and a transmission focus corresponding to the normal transmission and reception is formed in the region other than the ROI is performed. Thereby, it is possible to shorten the time required for the transmission and reception for sound speed setting in response to the instruction to set an ROI, while enhancing the image quality in the ROI.

Similarly to the above, reception data obtained by such transmission and reception is sequentially stored in the reception data memory 36. If reception data is stored in the reception data memory 36, first, the signal processor 20 reads reception data inside the ROI, and updates the optimum sound speed in the ROI in the same way as described above.

After the optimum sound speed in the ROI is updated, next, the signal processor 20 reads reception data from the reception data memory 36, and performs delay correction to produce a B-mode image signal. At this time, regarding reception data inside the ROI, delay correction is performed on the basis of the updated optimum sound speed, and regarding reception data in the region other than the ROI, delay correction is performed on the basis of the optimum sound speed used before the ROI determination. Thereafter, the B-mode image is displayed on the display unit 30 in a similar way to that described above.

In subsequent frames, the normal transmission and reception shown in FIG. 3A is performed at a predetermined frame rate, and reception data is processed to produce a B-mode image signal. Here, reception data inside the ROI is processed on the basis of the updated optimum sound speed, and reception data in the region other than the ROI is processed on the basis of the optimum sound speed used before the determination of the ROI. The B-mode image is displayed at a predetermined frame rate.

In the ultrasound diagnostic apparatus 10, for example, movement of the set ROI and the extension and reduction of the set ROI can be performed by operation instructions through the DELETE button 100, the trackball 102, and the SET button 106.

For example, as conceptually shown on an upper side of FIG. 9A, it is assumed that movement of the ROI is instructed, the ROI is moved, and the ROI is determined by the SET button 106. In response to this determination of the ROI, as shown on a lower side of FIG. 9A, the transmission and reception as above, in which a focus for setting is formed in the ROI and a transmission focus corresponding to the normal transmission and reception is formed in the region other than the ROI, is performed in the frame immediately after the determination according to the moved and determined ROI. Thereby, the optimum sound speed in the ROI is updated, and a B-mode image signal is produced and displayed.

Subsequently, the normal transmission and reception shown in FIG. 3A is performed at a predetermined frame rate, reception data is processed to produce a B-mode image signal, and the B-mode image is displayed. Here, reception data inside the ROI is processed on the basis of the updated optimum sound speed, and reception data in the region other than the ROI is processed on the basis of the optimum sound speed used before the determination of the ROI.

As conceptually shown on an upper side of FIG. 9B, it is assumed that the extension of the ROI (the extension of the ROI box) is instructed, and the ROI is extended and determined. In response to this extension and determination of the ROI, as shown on a lower side of FIG. 6B, the transmission and reception, in which a focus for setting and a transmission focus corresponding to the normal transmission and reception are formed, is performed in the frame immediately after the determination according to the extended and determined ROI in a manner similar to the above, the optimum sound speed in the ROI is updated, and a B-mode image is produced and displayed.

Subsequently, similarly to the above, the normal transmission and reception shown in FIG. 3A is performed at a predetermined frame rate, reception data is processed to produce a B-mode image signal, and the B-mode image is displayed. Reception data inside the ROI is processed on the basis of the updated optimum sound speed, and reception data in the region other than the ROI is processed on the basis of the optimum sound speed used before the determination of the ROI.

When the reduction of the ROI is performed, the update of the optimum sound speed may be performed similarly, or since the update of the optimum sound speed in the ROI has been performed at the time of ROI setting, the update of the optimum sound speed in the ROI may not be performed.

In the above example, when the determination of the ROI is instructed by determination means (determination instruction inputter), the transmission and reception for sound speed setting is performed, and the update of the optimum sound speed in the ROI is performed.

Here, even in a state where the determination is not instructed by the SET button 106, when there is no movement of the frame representing the ROI or no change in size thereof in a state where the setting, movement, extension, reduction or the like of the ROI is instructed, it is considered that the operator has an interest in the region as represented by the frame. That is, when the frame representing the ROI stops, it is considered that the operator has an interest in the region as represented by the frame.

Accordingly, in the invention, in a state where the setting, movement, extension, reduction or the like of the ROI is instructed, and before the determination of the ROI, when the ROI box stops for a predetermined time (for example, a predetermined time set appropriately between 0.5 to 5 seconds, in particular, about 1 second) or more, this may be regarded as the instruction to determine the ROI, and the update of the optimum sound speed in the box (or the entire ultrasound image) may be performed.

Alternatively, when the updated state of the optimum sound speed according to either the update of the optimum sound speed by the determination of the ROI or the update of the optimum sound speed according to the stopping of the frame representing the ROI is reached, the update of the optimum sound speed may be performed.

Further, two or more of the update of the optimum sound speed by the determination of the ROI, the update of the optimum sound speed according to the stopping of the ROI box, and the update of the optimum sound speed according to either the determination or the stopping of the ROI may be selected.

As above, according to the invention, in the ultrasound diagnostic apparatus, when the instruction on an observation target range, such as an instruction to change in observation depth or set an ROI, is given, the transmission and reception for sound speed setting is performed in response to this instruction to update a sound speed, and thereafter, delay correction is performed on the basis of the updated sound speed to produce a B-mode image.

Therefore, according to the invention, it is possible to stably display a high-quality ultrasound image with no distortion or the like on the basis of an accurate sound speed, correspondingly to an observation target range in which an ultrasound image is desired to be observed in detail.

In the ultrasound diagnostic apparatus 10, as shown on an upper side of FIG. 9C, it is possible to enlarge (and reduce) an ultrasound image inside the ROI using the ZOOM button 82 of the operating device 46.

In this case, the inside of the ROI is just enlarged and displayed, and as shown on a lower side of FIG. 9C, no instruction is given on an observation target range. Accordingly, when the enlargement of the ultrasound image inside the ROI is performed, in particular, the update of the optimum sound speed may not be performed.

However, when the ultrasound image inside the ROI is enlarged, it is considered that this is to observe the ROI in more detail.

For this reason, when the enlargement of the ultrasound image inside the ROI is performed, transmission and reception for sound speed setting in which the density of the focuses for setting in the ROI is higher than the density of the focuses for setting in the transmission and reception for setting shown in FIG. 3B may be performed in response to this instruction so as to update the sound speed in the ROI.

For example, as shown in FIG. 9C, if a displayed image becomes approximately an image inside the ROI by the enlargement of the ultrasound image, the transmission and reception for sound speed setting is performed so that five focuses for setting are formed for one scan line in the ROI. Accordingly, in regard to one scan line, it is possible to perform the update of the optimum sound speed in the ROI more closely with the same number of times of transmission as the transmission and reception for sound speed setting shown in FIG. 3B.

As described above, in the ultrasound diagnostic apparatus 10, the update of the optimum sound speed is performed at a regular timing of once for every predetermined number of frames.

At this time, in a state where the ROI is set as shown in FIGS. 8A and 8B or 9A to 9C, a regular update of the optimum sound speed may be performed only in the ROI or may be performed over the entire surface of the ultrasound image. However, if the update of the optimum sound speed only in the ROI is continued over a long time (in multiple frames), a sense of discomfort may arise between ultrasound images inside and outside the ROI. For this reason, even when the regular update of the optimum sound speed is performed only in the ROI, it is preferable to perform the update of the optimum sound speed over the entire surface of the ultrasound image at a frequency lower than the frequency of the update in the ROI.

In the above example, although change in observation depth and ROI setting are illustrated as the instruction on an observation target range, the invention is not limited thereto.

For example, as the instruction on an observation target range, extension and reduction of an observation region (observation field) in the azimuth direction, extension and reduction of an observation region (observation field) in both the azimuth direction and the depth direction, enlargement and reduction (zoom-in and zoom-out) of an ultrasound image, or the like may be used. Accordingly, instruction means (instruction inputter) for instructing the observation target range may be provided in the operating device 46, and in response to the instruction on an observation target range given by the instruction means, the transmission and reception for sound speed setting may be performed, the optimum sound speed may be updated, and thereafter, an ultrasound image may be produced.

In the ultrasound diagnostic apparatus 10 of the illustrated example, even in a state where the normal transmission and reception shown in FIG. 3A is repeatedly performed at a predetermined frame rate, and the B-mode image in the live mode is displayed, if change in image is instructed by operation through the operating device 46, in response to this instruction, the transmission and reception for sound speed setting is performed, and the update of the optimum sound speed is performed.

In the ultrasound diagnostic apparatus 10, it is assumed that in a state where the normal transmission and reception shown in FIG. 3A is performed at a predetermined frame rate, and a motion image in the live mode is displayed, the GAIN dial 114 is operated to give an instruction to change a gain. In response to this instruction, the controller 42 gives an instruction to the transmission circuit 16 and the reception circuit 18 so that the piezoelectric element array 14 performs the transmission and reception for sound speed setting shown in FIG. 3B in the transmission and reception immediately after the instruction to change a gain is given, and similarly to the above, the sound speed setter 40 sets the optimum sound speed and performs the update of the optimum sound speed.

Figure 10A:
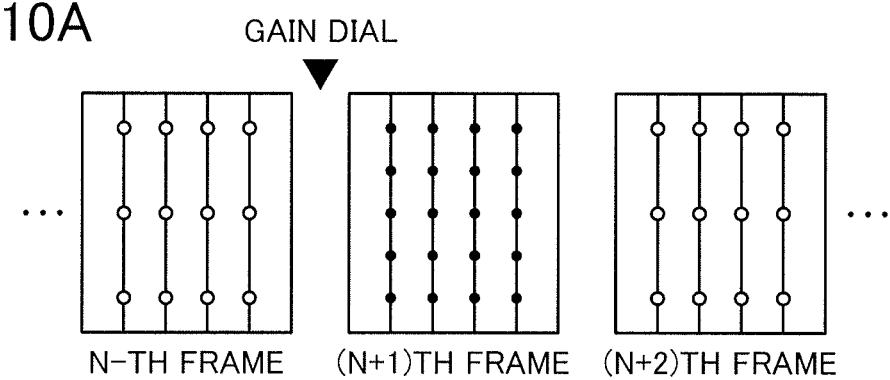
FIGS. 10A and 10B are conceptual diagrams illustrating another example of update of a sound speed in the ultrasound diagnostic apparatus shown in FIG. 1.

That is, as conceptually shown in FIG. 10A, in the ultrasound diagnostic apparatus 10, in the above-mentioned state where the normal transmission and reception shown in FIG. 3A is performed at a predetermined frame rate, and the B-mode image is displayed, if change in gain is performed in the N-th frame by the GAIN dial 114, the transmission and reception for sound speed setting shown in FIG. 3B is performed in the next (N+1)th frame in response to this instruction.

Figure 10B:
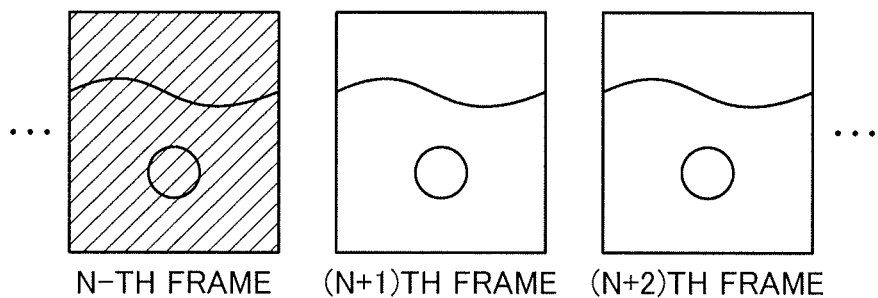

FIG. 10B conceptually shows ultrasound images which are produced by transmission and reception of an ultrasonic wave in individual frames.

After the transmission and reception for sound speed setting is performed in the (N+1)th frame immediately after the GAIN dial 114 is operated, similarly to the above, reception data is stored in the reception data memory 36, the signal processor 20 reads reception data from the reception data memory 36, and the optimum sound speed is set by the sound speed setter 40.

The sound speed setter 40 supplies the newly set optimum sound speed to the signal processor 20, and the signal processor 20 updates the optimum sound speed. That is, in the ultrasound diagnostic apparatus 10, as a preferred embodiment, the transmission and reception for sound speed setting is performed immediately after gain change is instructed, and the optimum sound speed is updated.

After the optimum sound speed is updated, the signal processor 20 reads reception data by the transmission and reception for sound speed setting from the reception data memory 36 again, and performs delay correction on the basis of the updated optimum sound speed to produce a B-mode image signal. When producing the B-mode image signal, thinning or the like of reception data may be performed as necessary.

The B-mode image signal produced by the signal processor 20 is processed in the DSC 24 and the image processor 26, and is displayed on the display unit 30.

In the subsequent (N+2)th frame and afterward, as shown in FIGS. 10A and 10B, the normal transmission and reception shown in FIG. 3A is performed, and reception data is processed on the basis of the updated optimum sound speed to produce a B-mode image signal.

In the ultrasound diagnostic apparatus 10 of the illustrated example, also when the STC key 68 is operated, in response thereto, the transmission and reception for sound speed setting is performed, and the update of the optimum sound speed is performed.

As described above, the STC key 68 is operating means (operating unit) which performs gain adjustment for each depth region of the ultrasound image, individually. In the illustrated example, the STC key 68 can adjust the gain in each of six depth regions, individually.

Figure 11A:
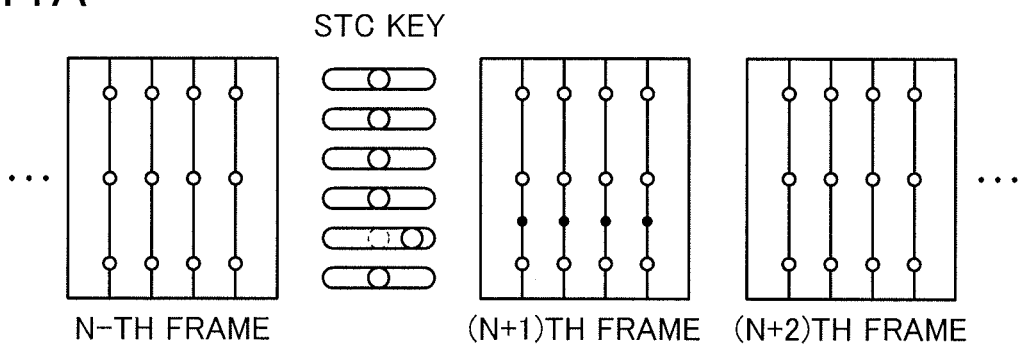
FIGS. 11A and 11B are conceptual diagrams illustrating another example of update of a sound speed in the ultrasound diagnostic apparatus shown in FIG. 1.

As conceptually shown in FIG. 11A, in the ultrasound diagnostic apparatus 10, similarly to the above, in the above-mentioned state where the normal transmission and reception shown in FIG. 3A is performed at a predetermined frame rate, and the B-mode image is displayed, if the STC key 68 is operated in the N-th frame to change the gain at any depth, the transmission and reception for sound speed setting shown in FIG. 3B is performed in the next (N+1)th frame.

Figure 11B:
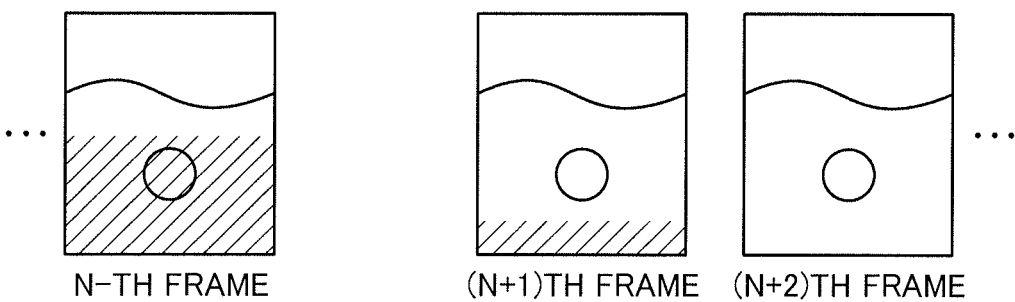

Similarly to FIG. 10B, FIG. 11B conceptually shows ultrasound images which are produced by transmission and reception of an ultrasonic wave in individual frames.

In this example, it is assumed that the second STC key 68 from the bottom (for the second deepest depth region) is operated.

The transmission and reception for sound speed setting in the (N+1)th frame corresponding to operation of the STC key 68 may be the transmission and reception for sound speed setting shown in FIG. 3B in which focuses for setting are formed over the entire surface of an ultrasound image, and the update of the optimum sound speed over the entire surface is performed.

However, a depth region in which the gain is not adjusted is a region for which the operator determines that image quality of the ultrasound image has no problem. Accordingly, in this depth region, it is not necessary to dare to perform the update of the optimum sound speed.

For this reason, in the transmission and reception for sound speed setting corresponding to operation of the STC key 68, as shown in FIG. 11A, the transmission and reception for sound speed setting is performed so that a focus for setting is only formed correspondingly to the depth region in which the gain is adjusted, and the same transmission focuses as those in the normal transmission and reception are formed in the other depth regions. Thereby, it is possible to shorten the time required for the transmission and reception for sound speed setting in response to the instruction to change a gain, while enhancing the image quality of the image in the depth region in which the gain is changed.

After the transmission and reception for sound speed setting is performed in the transmission and reception in the (N+1)th frame immediately after the STC key 68 is operated, similarly to the above, reception data is stored in the reception data memory 36. The signal processor 20 reads reception data obtained by the transmission to and reception from the transmission focus for sound speed update from the reception data memory 36. Using the read reception data, the sound speed setter 40 sets the optimum sound speed in the region in which the transmission focus for sound speed update is set, that is, the depth region for which change in gain is instructed.

The sound speed setter 40 supplies the newly set optimum sound speed to the signal processor 20, and the signal processor 20 updates the optimum sound speed of the depth region in which change in gain is instructed. That is, also in this example, as a preferred embodiment, the transmission and reception for sound speed setting is performed immediately after gain change is instructed by the STC key 68, and the optimum sound speed is updated.

After the optimum sound speed is updated, the signal processor 20 reads reception data, which is obtained by the transmission to and reception from the transmission focuses for B mode production in the transmission and reception for sound speed setting, from the reception data memory 36, and performs delay correction on the basis of the updated optimum sound speed to produce a B-mode image signal.

The B-mode image signal produced by the signal processor 20 is processed in the DSC 24 and the image processor 26, and is displayed on the display unit 30.

In the (N+2)th frame and afterward, as shown in FIGS. 11A and 11B, the normal transmission and reception shown in FIG. 3A is performed, and reception data is processed on the basis of the updated optimum sound speed to produce a B-mode image signal.

As described above, according to the invention, in the ultrasound diagnostic apparatus, in response to the instruction to change image quality, the transmission and reception for sound speed setting is performed immediately after the change in image quality is instructed to update the sound speed, and an ultrasound image is produced on the basis of the updated sound speed.

Therefore, according to the invention, it is possible to produce an ultrasound image at an accurate sound speed by updating a sound speed at an appropriate timing when the operator wants to improve image quality, and thus to produce a high-quality ultrasound image with no deterioration of image quality due to distortion or the like.

In clinical practice, during diagnosis, if a plurality of switches should be operated by the operator, this may cause erroneous operation. Accordingly, an increase in the number of switches to be operated during diagnosis causes a problem. In contrast, in the invention, the sound speed is updated with the instruction to change image quality as a trigger. Therefore, according to the invention, it is possible to update the sound speed at an appropriate timing without providing a switch which instructs to update a sound speed, so as to produce an ultrasound image of high-quality.

In the above example, the update of the optimum sound speed is performed when either of the GAIN dial 114 and the STC key 68 is operated. However, the invention is not limited thereto.

That is, in the invention, the optimum sound speed may be updated only when operation is performed corresponding to either the GAIN dial 114 or the STC key 68. Alternatively, selection means (selection instruction inputter) may be provided in the operating device 46, and any of the update of the optimum sound speed corresponding to operation of either of the GAIN dial 114 and the STC key 68, the update of the optimum sound speed corresponding to operation of only the GAIN dial 114, and the update of the optimum sound speed corresponding to operation of only the STC key 68 may be selected.

Further, in the ultrasound diagnostic apparatus 10 of the illustrated example, the transmission and reception for sound speed setting is performed at the timing when operation of the GAIN dial 114 or the STC key 68 starts. However, the invention is not limited thereto.

For example, the transmission and reception for sound speed setting may be performed at the timing when operation of the GAIN dial 114 or the STC key 68 is determined. Alternatively, the inventive apparatus may be configured such that the transmission and reception for sound speed setting is performed when operation of the GAIN dial 114 or the STC key 68 starts, and the update of the optimum sound speed is performed using reception data obtained by the preceding transmission and reception for sound speed setting at the timing when operation of the GAIN dial 114 or the STC key 68 is determined. In addition, the inventive apparatus may be configured such that when the amount of operation of the GAIN dial 114 or the STC key 68 exceeds a predetermined threshold value, the transmission and reception for sound speed setting is performed to update the optimum sound speed. These configurations may be selected by the mode or the like.

In the above example, as the instruction to change image quality of an ultrasound image that is accompanied with the update of the optimum sound speed, gain adjustment is illustrated.

However, in the ultrasound diagnostic apparatus 10 of the invention, the operating device 46 may additionally have at least one of dynamic range (contrast) adjustment means (adjustment instruction inputter), gradation curve processing (map) adjustment means (gradation curve processing instruction inputter), sharpness adjustment means (adjustment instruction inputter), and speckle noise removal processing instruction means (speckle noise removal processing instruction inputter), and when change (adjustment) in image quality is instructed corresponding to at least one of dynamic range, sharpness, gradation curve processing and speckle noise removal processing of an ultrasound image, the update of the optimum sound speed may be performed. Out of these instructions to change image quality, any may be selected as an instruction accompanied with the update of the optimum sound speed.

In the ultrasound diagnostic apparatus 10 of the invention, such changes in image quality may be performed using known image processing or the like. Further, such changes in image quality may be performed on the entire ultrasound image or carried out through means having a function of performing adjustment for each of predetermined depth regions, such as the STC key 68.

Further, in the ultrasound diagnostic apparatus 10, in the above-mentioned state where the normal transmission and reception shown in FIG. 3A is repeatedly performed in accordance with a predetermined frame rate, and B-mode image in the live mode is displayed, also when the instruction to change the image mode is given by operation of the operating device 46, the transmission and reception for sound speed setting is performed, and the update of the optimum sound speed is performed.

In the ultrasound diagnostic apparatus 10, it is assumed that in a state where the normal transmission and reception of FIG. 3A in a fundamental wave mode (hereinafter, also referred to as "FI mode") is performed at a predetermined frame rate, and a motion image in the live mode is displayed, the HARMONICS button 80 is pressed to instruct to switch the image mode to the THI mode. In response to this instruction, the controller 42 gives an instruction to the transmission circuit 16 and the reception circuit 18 so that the piezoelectric element array 14 performs the transmission and reception for sound speed setting of FIG. 3B in the THI mode in the transmission and reception immediately after the change in mode is instructed, and similarly to the above, the sound speed setter 40 sets the optimum sound speed and updates the optimum sound speed.

Figure 12A:
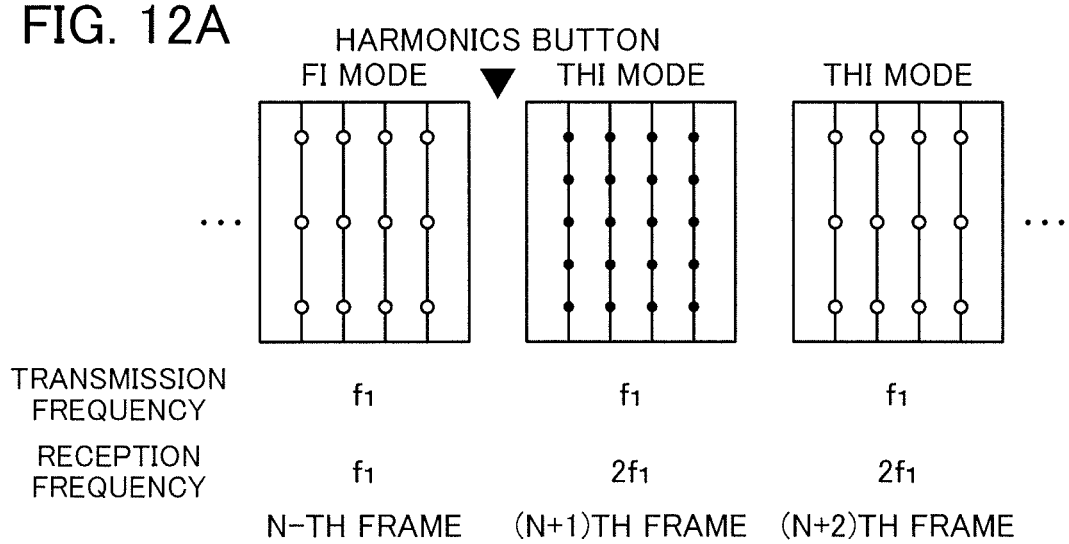
FIGS. 12A and 12B are conceptual diagrams illustrating another example of update of a sound speed in the ultrasound diagnostic apparatus shown in FIG. 1.

That is, in the ultrasound diagnostic apparatus 10, as conceptually shown in FIG. 12A, in a state where the normal transmission and reception of FIG. 3A in the FI mode (at a frequency of $f_1$ in both transmission and reception) is performed at a predetermined frame rate, and the B-mode image is displayed, if the HARMONICS button 80 is pressed in the N-th frame and change to the THI mode is performed, in response to this instruction, the transmission and reception for sound speed setting shown in FIG. 3B is performed in the next (N+1)th frame in the THI mode in which an ultrasonic wave (fundamental wave) at a frequency of $f_1$ is transmitted and an ultrasonic echo as a harmonic of the fundamental wave (e.g., a second harmonic (at a frequency of $2f_1$)) is received.

Figure 12B:
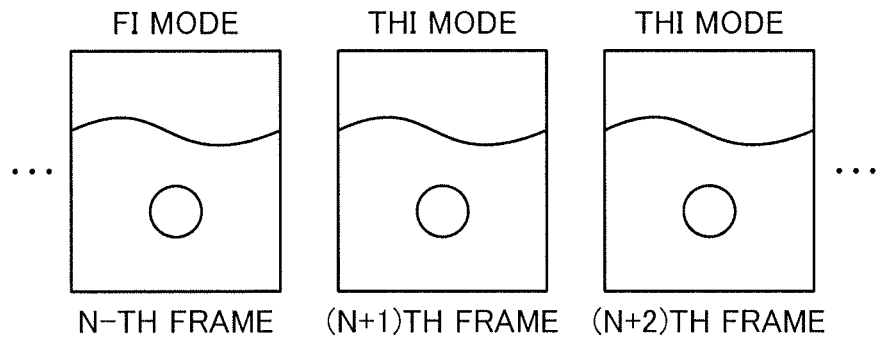

FIG. 12B conceptually shows ultrasound images which are produced by transmission and reception of an ultrasonic wave in individual frames.

After the transmission and reception for sound speed setting is performed in the transmission and reception in the (N+1)th frame immediately after the change to the THI mode is instructed, similarly to the above, reception data is stored in the reception data memory 36, the signal processor 20 reads reception data from the reception data memory 36, and the optimum sound speed is set by the sound speed setter 40.

The sound speed setter 40 supplies the newly set optimum sound speed to the signal processor 20, and the signal processor 20 updates the optimum sound speed. That is, in the ultrasound diagnostic apparatus 10, as a preferred embodiment, the transmission and reception for sound speed setting is performed immediately after the change to the THI mode is instructed, and the optimum sound speed is updated.

After the optimum sound speed is updated, the signal processor 20 reads reception data by the transmission and reception for sound speed setting from the reception data memory 36 again, and performs delay correction on the basis of the updated optimum sound speed to produce a B-mode image signal. When producing the B-mode image signal, thinning or the like of reception data may be performed as necessary.

The B-mode image signal produced by the signal processor 20 is processed in the DSC 24 and the image processor 26, and is displayed on the display unit 30.

In the (N+2)th frame and afterward, as shown in FIGS. 12A and 12B, the normal transmission and reception shown in FIG. 3A is performed in the THI mode in which the ultrasonic wave at a frequency of $f_1$ is transmitted and the ultrasonic echo as a second harmonic of the fundamental wave that has a frequency of $2f_1$ is received, and reception data is processed on the basis of the updated optimum sound speed to produce the B-mode image signal in the THI mode.

Further, in the ultrasound diagnostic apparatus 10, also when mode change from the FI mode to the CH mode is performed, similarly to the above, the update of the optimum sound speed is performed.

Figure 13A:
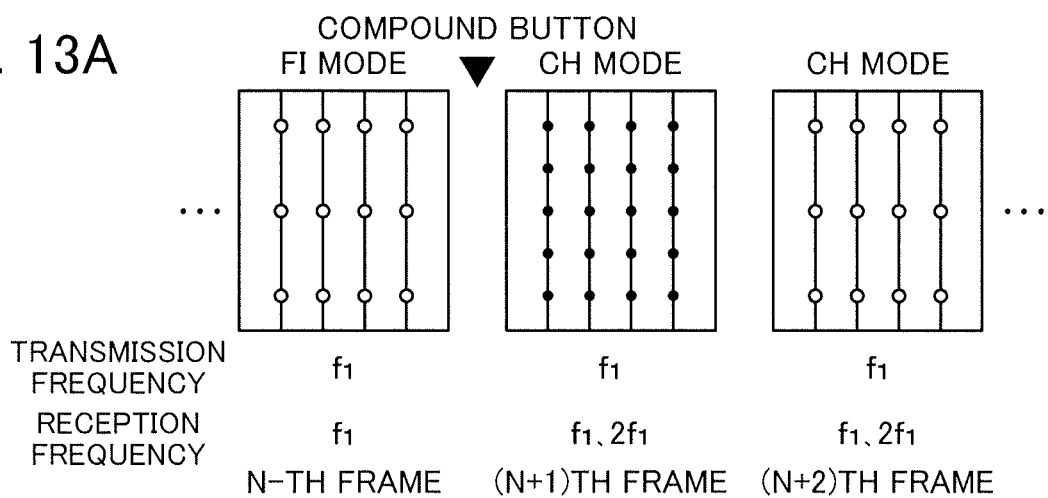
FIGS. 13A and 13B are conceptual diagrams illustrating another example of update of a sound speed in the ultrasound diagnostic apparatus shown in FIG. 1.

That is, as conceptually shown in FIG. 13A, in the ultrasound diagnostic apparatus 10, it is assumed that in a state where the normal transmission and reception of FIG. 3A in the FI mode (at a frequency of $f_1$ in both transmission and reception) is performed at a predetermined frame rate, and the B-mode image is displayed, the COMPOUND button 78 is pressed in the N-th frame to instruct to change the image mode to the CH mode. In response to this instruction, the transmission and reception for sound speed setting shown in FIG. 3B is performed in the next (N+1)th frame in the CH mode in which an ultrasonic wave at a frequency of $f_1$ is transmitted, and an ultrasonic echo as a fundamental wave at a frequency of $f_1$ and an ultrasonic echo as a harmonic of the fundamental wave (e.g., a second harmonic (at a frequency of $2f_1$)) are received.

Figure 13B:
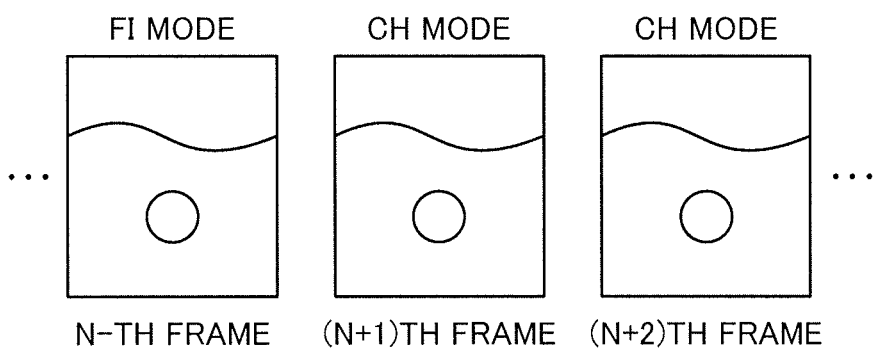

FIG. 13B conceptually shows ultrasound images which are produced by transmission and reception of an ultrasonic wave in individual frames.

After the transmission and reception for sound speed setting is performed in the transmission and reception in the (N+1)th frame immediately after the change to the CH mode is instructed, similarly to the above, reception data is stored in the reception data memory 36, the signal processor 20 reads reception data from the reception data memory 36, and the optimum sound speed is set by the sound speed setter 40.

The sound speed setter 40 supplies the newly set optimum sound speed to the signal processor 20, and the signal processor 20 updates the optimum sound speed.

After the optimum sound speed is updated, the signal processor 20 reads reception data by the transmission and reception for sound speed setting from the reception data memory 36 again, and performs delay correction on the basis of the updated optimum sound speed to produce a B-mode image signal. The B-mode image signal produced by the signal processor 20 is processed in the DSC 24 and the image processor 26, and is displayed on the display unit 30.

In the (N+2)th frame and afterward, as shown in FIGS. 13A and 13B, the normal transmission and reception shown in FIG. 3A is performed in the CH mode in which the ultrasonic wave at a frequency of $f_1$ is transmitted, and the ultrasonic echo at a frequency of $f_1$ and the ultrasonic echo as the second harmonic at a frequency of $2f_1$ of the fundamental wave are received, and reception data is processed on the basis of the updated optimum sound speed to produce the B-mode image signal in the CH mode.

In the example shown in FIGS. 13A and 13B, in the CH mode, transmission of an ultrasonic wave is performed only once. However, the invention is not limited thereto, and in the CH mode, two (or more) transmissions of an ultrasonic wave may be performed, and the images obtained may be synthesized.

Figure 14A:
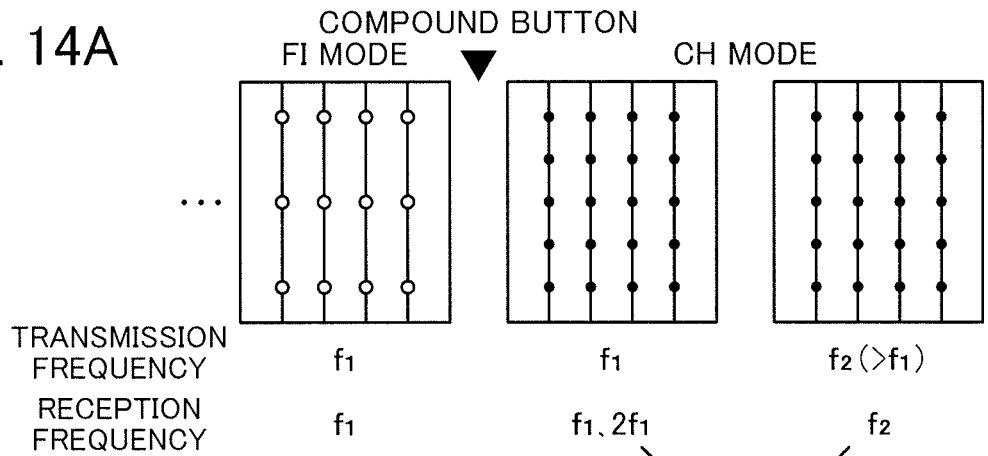
FIGS. 14A and 14B are conceptual diagrams illustrating an example of an image mode in the ultrasound diagnostic apparatus shown in FIG. 1.
Figure 14B:
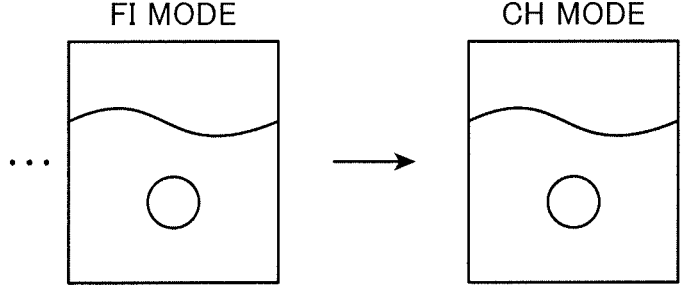

That is, as conceptually shown in FIGS. 14A and 14B, in a state where the normal transmission and reception of FIG. 3A in the FI mode is performed at a predetermined frame rate, and the B-mode image is displayed, if the COMPOUND button 78 is pressed to perform the change to the CH mode, in the CH mode, the transmission and reception, in which an ultrasonic wave at a frequency of $f_1$ is transmitted and ultrasonic echoes as a fundamental wave at a frequency of $f_1$ and as a harmonic at a frequency of $2f_1$ of the fundamental wave are received, and the transmission and reception, in which an ultrasonic wave at a frequency of $f_2$ ($f_1<f_2$) is transmitted and an ultrasonic echo at a frequency of $f_2$ is received, may be performed.

As described above, according to the invention, in the ultrasound diagnostic apparatus, in response to the instruction to change the image mode, the transmission and reception for sound speed setting is performed immediately after the change of the image mode is instructed to update the sound speed, and an ultrasound image is produced on the basis of the updated sound speed.

Therefore, according to the invention, it is possible to produce an ultrasound image at an accurate sound speed by updating the sound speed at an appropriate timing immediately after the image mode is changed, and thus to produce a high-quality ultrasound image with no deterioration of image quality due to distortion or the like immediately after the image mode is changed.

In the above example, as switching of the image mode, switching from the FI mode to the THI mode and switching from the FI mode to the CH mode are illustrated. In the ultrasound diagnostic apparatus 10, the transmission and reception for sound speed setting is performed so as to update the optimum sound speed also when switching from the THI mode to the FI mode, switching from the CH mode to the FI mode, switching from the THI mode to the CH mode, and switching from the CH mode to the THI mode are each instructed.

In a state where the B-mode image is displayed, when the B button 94 or the like is pressed, the transmission and reception for sound speed setting may similarly be performed so as to update the optimum sound speed.

In the above example, the optimum sound speed is updated correspondingly to all instructions to switch the image mode including switching from the FI mode to the THI mode, switching from the FI mode to the CH mode, switching from the THI mode to the FI mode, switching from the CH mode to the FI mode, switching from the THI mode to the CH mode, and switching from the CH mode to the THI mode.

However, the invention is not limited thereto. That is, in the invention, the update of the optimum sound speed may be performed correspondingly to only one or more out of the instructions to switch the image mode. The switching of the image mode accompanied with the update of the optimum sound speed may be selected by operation of the operating device 46 or the like.

Further, also when switching to so-called frequency compounding or spatial compounding is instructed, similarly, the update of the optimum sound speed may be performed.

Moreover, in the above example, when the display of the ultrasound image in the B mode is being performed, the update of the optimum sound speed is performed if the switching of the image mode is instructed.

However, in the ultrasound diagnostic apparatus 10 of the invention, the optimum sound speed may similarly be updated also in the case where, for instance, a similar switching of the image mode is performed when an ultrasound image is being displayed in the M mode. A display mode accompanied with the update of the optimum sound speed may be selected according to the switching of the image mode.

In the ultrasound diagnostic apparatus 10 of the illustrated example, when any instruction out of the instruction of freeze, the instruction on the observation target range, the instruction to change image quality, and the instruction to change the image mode is given, the transmission and reception for sound speed setting is performed, and the optimum sound speed is updated. However, the invention is not limited thereto.

For example, the update of the optimum sound speed may be performed correspondingly to only one instruction or only two or three instructions out of the instruction of freeze, the instruction on the observation target range, the instruction to change image quality, and the instruction to change the image mode. Furthermore, one or more instructions accompanied with the update of the optimum sound speed may be selected by mode selection or the like.

Further, in the above example, the transmission and reception for sound speed setting for updating the optimum sound speed is performed in one frame. However, the invention is not limited thereto. The formation of the focus for setting may be performed in plural frames, and the update of the optimum sound speed over the entire screen may be performed in the plural frames.

Figure 15A:
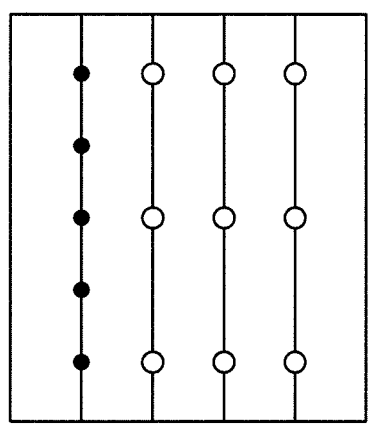
FIGS. 15A to 15D are conceptual diagrams illustrating another example of update of a sound speed in the ultrasound diagnostic apparatus shown in FIG. 1.

As an example, when performing the update (setting) of the optimum sound speed in response to each of the instructions described above, in the first frame, as shown in FIG. 15A, a focus for setting is formed only on the first scan line from the left of the drawing, and a transmission focus corresponding to the normal transmission and reception is formed on other scan lines, whereby the optimum sound speed is updated correspondingly to the focus for setting.

Figure 15B:
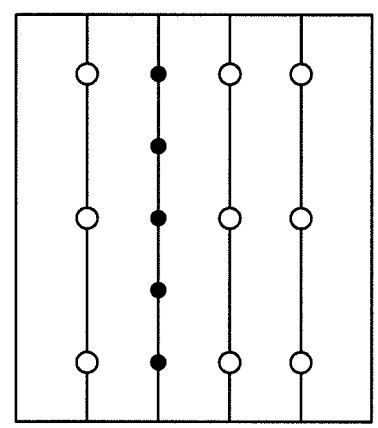

In the next, second frame, as shown in FIG. 15B, a focus for setting is formed only on the second scan line from the left of the drawing, and a transmission focus corresponding to the normal transmission and reception is formed on other scan lines, whereby the optimum sound speed is updated correspondingly to the focus for setting.

Figure 15C:
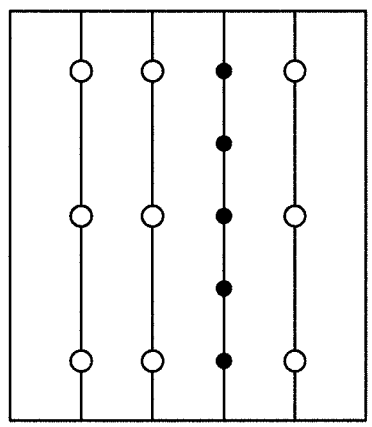

In the next, third frame, as shown in FIG. 15C, a focus for setting is formed only on the third scan line from the left of the drawing, and a transmission focus corresponding to the normal transmission and reception is formed on other scan lines, whereby the optimum sound speed is updated correspondingly to the focus for setting.

Figure 15D:
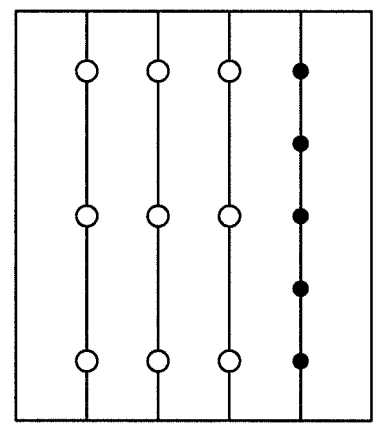

In the next, fourth frame, as shown in FIG. 15D, a focus for setting is formed only on the fourth scan line from the left of the drawing, and a transmission focus corresponding to the normal transmission and reception is formed on other scan lines, whereby the optimum sound speed is updated correspondingly to the focus for setting. In this way, the optimum sound speed may be updated over the entire screen (the entire surface of an ultrasound image) in four frames in total.

Alternatively, a focus for setting may be formed for each depth, instead of each scan line, so as to update the optimum sound speed at one depth in one frame. For example, in the example shown in FIG. 3B, focuses for setting may be sequentially formed in ascending order of the depth, with a focus for setting at one depth being formed in one frame, and the optimum sound speed may be updated over the entire screen in five frames.

Furthermore, one or plural focuses for setting may be formed in one frame, and the update of the optimum sound speed may be performed for each focus for setting. For example, in the example shown in FIG. 3B, one focus for setting may be formed in one frame, and the optimum sound speed may be updated over the entire screen in 20 frames.

So far, the ultrasound diagnostic apparatus, the method of producing an ultrasound image, and the recording medium of the invention have been described in detail based on the examples, but the invention is not limited thereto, and various improvements and modifications may be of course made without departing from the gist of the invention.

The invention can be suitably used for ultrasound diagnosis which is used for various kinds of diagnoses in clinical practice or the like.

What is claimed is:

1. An ultrasound diagnostic apparatus comprising:
   a piezoelectric element array which has piezoelectric elements arranged therein, each piezoelectric element configured to transmit an ultrasonic wave, to receive an ultrasonic echo reflected by a subject, and to output a reception signal according to a received ultrasonic wave;
   a controller which controls ultrasonic transmission and reception by the piezoelectric element array;
   a storage which stores the reception signal output from the piezoelectric element array;
   a sound speed setter which sets a sound speed in the subject using the reception signal stored in the storage;
   an image producer which processes the reception signal output from the piezoelectric element array or the reception signal read from the storage, based on the sound speed set by the sound speed setter to produce an ultrasound image;
   a display; and
   an operating device which has a freeze instruction inputter configured to instruct to display a still image on the display, an observation target range instruction inputter configured to specify an observation target range of an ultrasound image displayed on the display, an image quality change instruction inputter configured to instruct to change image quality of the ultrasound image, and a mode change instruction inputter configured to instruct to change an image mode of the ultrasound image, wherein the controller causes the piezoelectric element array to perform ultrasonic transmission and reception for sound speed setting so as to allow the sound speed setter to set the sound speed in response to at least one instruction out of an instruction to display a still image from the freeze instruction inputter, an instruction on the observation target range from the observation target range instruction inputter, an instruction to change image quality from the image quality change instruction inputter, and an instruction to change an image mode from the mode change instruction inputter, the sound speed setter sets the sound speed in the subject using a reception signal obtained by the ultrasonic transmission and reception for sound speed setting to update the sound speed, the image producer processes the reception signal output from the piezoelectric element array based on an updated sound speed to produce an ultrasound image, the display displays the ultrasound image produced by processing based on the updated sound speed, the observation target range instruction inputter further includes an observation depth change instruction inputter configured to instruct change in observation depth, and the observation depth change instruction inputter has an extension and reduction instruction inputter configured to increase and decrease the observation depth, and the sound speed setter updates the sound speed only for a region extended or reduced through the extension and reduction instruction inputter configured to increase and decrease the observation depth.

2. An ultrasound diagnostic apparatus comprising:

a piezoelectric element array which has piezoelectric elements arranged therein, each piezoelectric element configured to transmit an ultrasonic wave, to receive an ultrasonic echo reflected by a subject, and to output a reception signal according to a received ultrasonic wave;

a controller which controls ultrasonic transmission and reception by the piezoelectric element array;

a storage which stores the reception signal output from the piezoelectric element array;

a sound speed setter which sets a sound speed in the subject using the reception signal stored in the storage;

an image producer which processes the reception signal output from the piezoelectric element array or the reception signal read from the storage, based on the sound speed set by the sound speed setter to produce an ultrasound image;

a display; and an operating device which has a freeze instruction inputter configured to instruct to display a still image on the display, an observation target range instruction inputter configured to specify an observation target range of an ultrasound image displayed on the display, an image quality change instruction inputter configured to instruct to change image quality of the ultrasound image, and a mode change instruction inputter configured to instruct to change an image mode of the ultrasound image, wherein the controller causes the piezoelectric element array to perform ultrasonic transmission and reception for sound speed setting so as to allow the sound speed setter to set the sound speed in response to at least one instruction out of an instruction to display a still image from the freeze instruction inputter, an instruction on the observation target range from the observation target range instruction inputter, an instruction to change image quality from the image quality change instruction inputter, and an instruction to change an image mode from the mode change instruction inputter, the sound speed setter sets the sound speed in the subject using a reception signal obtained by the ultrasonic transmission and reception for sound speed setting to update the sound speed, the image producer processes the reception signal output from the piezoelectric element array based on an updated sound speed to produce an ultrasound image, the display displays the ultrasound image produced by processing based on the updated sound speed, the image quality change instruction inputter instructs to change image quality of the ultrasound image for a predetermined region, and when change in image quality for the predetermined region is instructed by the image quality change instruction inputter, the controller causes the piezoelectric element array to perform, with respect to the predetermined region, the ultrasonic transmission and reception for sound speed setting so as to allow the sound speed setter to set the sound speed, and the sound speed setter sets a sound speed in the predetermined region using the reception signal obtained by the ultrasonic transmission and reception for sound speed setting to update the sound speed.

3. An ultrasound diagnostic apparatus comprising:

a piezoelectric element array which has piezoelectric elements arranged therein, each piezoelectric element configured to transmit an ultrasonic wave, to receive an ultrasonic echo reflected by a subject, and to output a reception signal according to a received ultrasonic wave;

a controller which controls ultrasonic transmission and reception by the piezoelectric element array;

a storage which stores the reception signal output from the piezoelectric element array;

a sound speed setter which sets a sound speed in the subject using the reception signal stored in the storage;

an image producer which processes the reception signal output from the piezoelectric element array or the reception signal read from the storage, based on the sound speed set by the sound speed setter to produce an ultrasound image;

a display; and an operating device which has a freeze instruction inputter configured to instruct to display a still image on the display, an observation target range instruction inputter configured to specify an observation target range of an ultrasound image displayed on the display, an image quality change instruction inputter configured to instruct to change image quality of the ultrasound image, and a mode change instruction inputter configured to instruct to change an image mode of the ultrasound image, wherein the controller causes the piezoelectric element array to perform ultrasonic transmission and reception for sound speed setting so as to allow the sound speed setter to set the sound speed in response to at least one instruction out of an instruction to display a still image from the freeze instruction inputter, an instruction on the observation target range from the observation target range instruction inputter, an instruction to change image quality from the image quality change instruction inputter, and an instruction to change an image mode from the mode change instruction inputter, the sound speed setter sets the sound speed in the subject using a reception signal obtained by the ultrasonic transmission and reception for sound speed setting to update the sound speed, the image producer processes the reception signal output from the piezoelectric element array based on an updated sound speed to produce an ultrasound image, the display displays the ultrasound image produced by processing based on the updated sound speed, and wherein change in image quality of the ultrasound image according to the instruction to change image quality from the image quality change instruction inputter is performed by either or both of change of an amplification factor for amplifying the reception signal and image processing in the image producer.

4. The ultrasound diagnostic apparatus according to claim 2, wherein the image quality change instruction inputter has a function of instructing the change in image quality for each depth region set in advance, and when a depth region for which image quality is to be changed is specified by an instruction from the image quality change instruction inputter, the sound speed setter only updates the sound speed in the specified depth region.

5. An ultrasound diagnostic apparatus comprising:

a piezoelectric element array which has piezoelectric elements arranged therein, each piezoelectric element configured to transmit an ultrasonic wave, to receive an ultrasonic echo reflected by a subject, and to output a reception signal according to a received ultrasonic wave;

a controller which controls ultrasonic transmission and reception by the piezoelectric element array;

a storage which stores the reception signal output from the piezoelectric element array;

a sound speed setter which sets a sound speed in the subject using the reception signal stored in the storage;

an image producer which processes the reception signal output from the piezoelectric element array or the reception signal read from the storage, based on the sound speed set by the sound speed setter to produce an ultrasound image;

a display; and an operating device which has a freeze instruction inputter configured to instruct to display a still image on the display, an observation target range instruction inputter configured to specify an observation target range of an ultrasound image displayed on the display, an image quality change instruction inputter configured to instruct to change image quality of the ultrasound image, and a mode change instruction inputter configured to instruct to change an image mode of the ultrasound image, wherein the controller causes the piezoelectric element array to perform ultrasonic transmission and reception for sound speed setting so as to allow the sound speed setter to set the sound speed in response to at least one instruction out of an instruction to display a still image from the freeze instruction inputter, an instruction on the observation target range from the observation target range instruction inputter, an instruction to change image quality from the image quality change instruction inputter, and an instruction to change an image mode from the mode change instruction inputter, the sound speed setter sets the sound speed in the subject using a reception signal obtained by the ultrasonic transmission and reception for sound speed setting to update the sound speed, the image producer processes the reception signal output from the piezoelectric element array based on an updated sound speed to produce an ultrasound image, the display displays the ultrasound image produced by processing based on the updated sound speed, and the image quality change instruction inputter has at least one of a gain adjustment instruction inputter configured to adjust gain of an ultrasound image, a dynamic range adjustment instruction inputter configured to adjust dynamic range of an ultrasound image, a gradation curve processing instruction inputter configured to process gradation curve of an ultrasound image, a sharpness adjustment instruction inputter configured to adjust sharpness of an ultrasound image, and a speckle noise removal processing instruction inputter configured to instruct removal of speckle noise from an ultrasound image.

6. An ultrasound diagnostic apparatus comprising:

a piezoelectric element array which has piezoelectric elements arranged therein, each piezoelectric element configured to transmit an ultrasonic wave, to receive an ultrasonic echo reflected by a subject, and to output a reception signal according to a received ultrasonic wave;

a controller which controls ultrasonic transmission and reception by the piezoelectric element array;

a storage which stores the reception signal output from the piezoelectric element array;

a sound speed setter which sets a sound speed in the subject using the reception signal stored in the storage;

an image producer which processes the reception signal output from the piezoelectric element array or the reception signal read from the storage, based on the sound speed set by the sound speed setter to produce an ultrasound image;

a display; and an operating device which has a freeze instruction inputter configured to instruct to display a still image on the display, an observation target range instruction inputter configured to specify an observation target range of an ultrasound image displayed on the display, an image quality change instruction inputter configured to instruct to change image quality of the ultrasound image, and a mode change instruction inputter configured to instruct to change an image mode of the ultrasound image, wherein the controller causes the piezoelectric element array to perform ultrasonic transmission and reception for sound speed setting so as to allow the sound speed setter to set the sound speed in response to at least one instruction out of an instruction to display a still image from the freeze instruction inputter, an instruction on the observation target range from the observation target range instruction inputter, an instruction to change image quality from the image quality change instruction inputter, and an instruction to change an image mode from the mode change instruction inputter, the sound speed setter sets the sound speed in the subject using a reception signal obtained by the ultrasonic transmission and reception for sound speed setting to update the sound speed, the image producer processes the reception signal output from the piezoelectric element array based on an updated sound speed to produce an ultrasound image, the display displays the ultrasound image produced by processing based on the updated sound speed, and the image mode is any of a fundamental wave mode, a tissue harmonic mode, and a compound harmonic mode.

7. A method of producing an ultrasound image, the method comprising the steps of:

performing ultrasonic transmission and reception for sound speed setting so as to set a sound speed in a subject in response to at least one instruction out of an instruction to freeze to display a still image, an instruction on an observation target range of an ultrasound image, an instruction to change image quality of an ultrasound image, and an instruction to change an image mode of an ultrasound image;

setting the sound speed in the subject using a reception signal obtained by the ultrasonic transmission and reception for sound speed setting;

processing an ultrasonic reception signal based on the sound speed to produce an ultrasound image; and displaying the ultrasound image, wherein the instruction on an observation target range is an instruction of extension or reduction of the observation depth, and when extension or reduction of the observation depth is performed, setting of the sound speed is performed only for a region extended or reduced.

8. A method of producing an ultrasound image, the method comprising the steps of:

performing ultrasonic transmission and reception for sound speed setting so as to set a sound speed in a subject in response to at least one instruction out of an instruction to freeze to display a still image, an instruction on an observation target range of an ultrasound image, an instruction to change image quality of an ultrasound image, and an instruction to change an image mode of an ultrasound image;

setting the sound speed in the subject using a reception signal obtained by the ultrasonic transmission and reception for sound speed setting;

processing an ultrasonic reception signal based on the sound speed to produce an ultrasound image; and displaying the ultrasound image, wherein the instruction to change image quality is an instruction to change in image quality for each region set in advance, and when change in image quality for the region set in advance is instructed, the ultrasonic transmission and reception for setting the sound speed in the specified region is performed, and the sound speed for the region is set using a reception signal obtained by the ultrasonic transmission and reception for setting the sound speed.

9. A method of producing an ultrasound image, the method comprising the steps of:

performing ultrasonic transmission and reception for sound speed setting so as to set a sound speed in a subject in response to at least one instruction out of an instruction to freeze to display a still image, an instruction on an observation target range of an ultrasound image, an instruction to change image quality of an ultrasound image, and an instruction to change an image mode of an ultrasound image;

setting the sound speed in the subject using a reception signal obtained by the ultrasonic transmission and reception for sound speed setting;

processing an ultrasonic reception signal based on the sound speed to produce an ultrasound image; and displaying the ultrasound image, wherein change in image quality of the ultrasound image according to the instruction to change image quality is performed by either or both of change of an amplification factor for amplifying the reception signal and image processing when producing the ultrasound image.

10. A method of producing an ultrasound image, the method comprising the steps of:

performing ultrasonic transmission and reception for sound speed setting so as to set a sound speed in a subject in response to at least one instruction out of an instruction to freeze to display a still image, an instruction on an observation target range of an ultrasound image, an instruction to change image quality of an ultrasound image, and an instruction to change an image mode of an ultrasound image;

setting the sound speed in the subject using a reception signal obtained by the ultrasonic transmission and reception for sound speed setting;

processing an ultrasonic reception signal based on the sound speed to produce an ultrasound image; and displaying the ultrasound image, wherein change in image quality of the ultrasound image according to the instruction to change image quality is performed by at least one of a gain adjustment to adjust gain of an ultrasound image, a dynamic range adjustment to adjust dynamic range of an ultrasound image, a gradation curve processing to process gradation curve of an ultrasound image, a sharpness adjustment to adjust sharpness of an ultrasound image, and a speckle noise removal processing to remove speckle noise from an ultrasound image.

11. A method of producing an ultrasound image, the method comprising the steps of:

performing ultrasonic transmission and reception for sound speed setting so as to set a sound speed in a subject in response to at least one instruction out of an instruction to freeze to display a still image, an instruction on an observation target range of an ultrasound image, an instruction to change image quality of an ultrasound image, and an instruction to change an image mode of an ultrasound image;

setting the sound speed in the subject using a reception signal obtained by the ultrasonic transmission and reception for sound speed setting;

processing an ultrasonic reception signal based on the sound speed to produce an ultrasound image; and displaying the ultrasound image, wherein the image mode is any of a fundamental wave mode, a tissue harmonic mode, and a compound harmonic mode.

* * * * *